United States Patent
Pai et al.

(10) Patent No.: US 7,561,909 B1
(45) Date of Patent: Jul. 14, 2009

(54) MRI NAVIGATOR METHODS AND SYSTEMS

(75) Inventors: Vinay M. Pai, New York, NY (US); Han Wen, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 1507 days.

(21) Appl. No.: 10/244,903

(22) Filed: Sep. 16, 2002

(51) Int. Cl.
*A61B 5/05* (2006.01)

(52) U.S. Cl. .................. 600/410; 600/419; 324/307; 324/308

(58) Field of Classification Search .......... 600/410, 600/411, 413, 419, 407; 324/307, 308–309
See application file for complete search history.

(56) References Cited

U.S. PATENT DOCUMENTS

| | | | |
|---|---|---|---|
| 5,031,624 A * | 7/1991 | Mistretta et al. ........... 600/419 |
| 5,093,620 A | 3/1992 | Pelc et al. |
| 5,141,578 A * | 8/1992 | Yang .......................... 156/79 |
| 5,200,700 A | 4/1993 | Glover et al. |
| 5,285,158 A * | 2/1994 | Mistretta et al. ........... 324/309 |
| 5,382,902 A | 1/1995 | Taniguchi et al. |
| 5,427,101 A | 6/1995 | Sachs et al. |
| 5,512,825 A | 4/1996 | Atalar et al. |
| 5,517,117 A | 5/1996 | Mueller et al. |
| 5,602,891 A | 2/1997 | Pearlman |
| 5,766,128 A | 6/1998 | Halamek et al. |
| 5,800,354 A | 9/1998 | Hofland et al. |
| 5,842,989 A | 12/1998 | Zur |
| 6,031,374 A | 2/2000 | Epstein et al. |
| 6,057,685 A | 5/2000 | Zhou |
| 6,067,465 A | 5/2000 | Foo et al. |
| 6,073,041 A * | 6/2000 | Hu et al. .................... 600/410 |
| 6,141,578 A | 10/2000 | Hardy |
| 6,144,874 A | 11/2000 | Du |
| 6,171,241 B1 | 1/2001 | McVeigh et al. |
| 6,184,682 B1 | 2/2001 | Ehman et al. |
| 6,236,705 B1 | 5/2001 | Stergiopoulos et al. |
| 6,275,720 B1 | 8/2001 | Du et al. |
| 6,292,683 B1 | 9/2001 | Gupta et al. |
| 6,292,684 B1 * | 9/2001 | Du et al. .................... 600/410 |
| 6,307,369 B1 | 10/2001 | Felmlee et al. |

(Continued)

OTHER PUBLICATIONS

Yiping Du et al. "Respiratory displacement and velocity measurement using navigator MRI echo signals" Apr. 7, 2001, Europe Patent Office, EP 1113288 A2.*

(Continued)

*Primary Examiner*—Eric F Winakur
*Assistant Examiner*—Katherine L Fernandez
(74) *Attorney, Agent, or Firm*—Klarquist Sparkman, LLP

(57) ABSTRACT

Navigator methods are disclosed that are based on detecting a flow-sensitive signal within a subject, and using the position of the signal to track subject motion between imaging sequences. In a disclosed embodiment, the fast-moving blood volume in the left ventricle of the heart is detected and used as a reference point to correct for cardiac motion that results from respiratory motion in a subject. The navigator based on the position of the fast-moving blood volume in the left ventricle may be applied prospectively to shift a subsequent imaging slice to compensate for subject motion, and thereby provide MRI images with increased clarity and resolution.

31 Claims, 21 Drawing Sheets

U.S. PATENT DOCUMENTS

| | | |
|---|---|---|
| 6,329,819 B1 | 12/2001 | Manduca et al. |
| 6,377,831 B1 | 4/2002 | Seshan et al. |
| 6,380,739 B1 | 4/2002 | Machida |
| 6,393,313 B1 | 5/2002 | Foo |
| 6,516,210 B1 * | 2/2003 | Foxall .................. 600/410 |
| 6,552,542 B1 * | 4/2003 | Overall ................. 324/309 |
| 6,791,323 B2 * | 9/2004 | Wang et al. ........... 324/309 |
| 6,922,580 B2 * | 7/2005 | DeMeester et al. ...... 600/413 |
| 2001/0038285 A1 | 11/2001 | Zhu |

OTHER PUBLICATIONS

Yi Wang et al. "Respiratory Motion of the Heart: Kinematics and the Implications for the Spatial Resolution in Coronary Imaging", 1995, Magnetic Resonance in Medicine, vol. 33:713-719.*

* cited by examiner

MRI NAVIGATOR METHODS AND SYSTEMS

FIELD

The disclosure relates generally to magnetic resonance imaging (MRI). In particular, the disclosure relates to navigator methods for reducing MRI image artifacts that are due to subject motion, such as respiratory motion, during acquisition of a MR image.

BACKGROUND

During magnetic resonance image acquisition, subject motion can lead to artifacts, intensity loss, and lowered sharpness that degrade the clarity with which lesions and anatomic details can be depicted. For example, cardiac imaging sequences often span multiple heartbeats to obtain the necessary temporal and spatial resolutions. Under such conditions, motion artifacts due to respiratory motion can significantly impair the quality of the MR images (MRIs).

A number of techniques have been proposed and developed over the years to minimize the effects of motion, particularly respiratory motion, on MR images. Breath-hold techniques and navigator methods are among these approaches. Each of these techniques has its own inherent advantages and limitations. For example, breath-holding, the simplest and most commonly used approach to reducing motion artifacts, limits the available scan time and may induce physiological changes during the course of a breath-hold.

Navigator methods, on the other hand, allow normal or quiet breathing and require less patient coaching. They greatly extend the available scan time and help maintain a normal physiologic state. However, it is often difficult to accurately measure the position of organs such as the heart in real-time.

A typical MRI navigator approach to compensating for respiratory motion during cardiac imaging utilizes an excitation profile that crosses the diaphragm and generates a signal that may be used to track the superior-inferior motion (head-to-toe motion) of the diaphragm. The position of the diaphragm at its interface with the lungs is detected by the navigator signal and used to determine the heart location. Since respiratory motion of the heart is dominated by a superior-inferior (SI) component that is approximately linearly correlated to the SI motion of the diaphragm the position of the heart may be estimated. However, this approach necessitates a priori knowledge of the correlation coefficient between heart and diaphragm motion, a variable parameter among patients and different portions of the heart. For example, in one study the mean correlating factors amongst patients for the right coronary artery (RCA) root and the left anterior descending (LAD) artery vis-à-vis the SI position of the diaphragm were determined to be 0.57±0.26 (standard deviation (SD)) and 0.70±0.18 (SD), respectively.

Recent research shows that there is also an anterior-posterior (AP) movement of the heart that is correlated with movement of the diaphragm, but again in patient-specific ways. Application of navigators to the free wall of the left ventricle (LV wall) is more reliable for detecting AP motion. However, LV wall navigators have the disadvantage that magnetization voids can occur at the lung-LV free wall interface, and using a smaller diameter navigator to compensate reduces the signal-to-noise ratio (SNR) of the navigator. Application of pencil-beam navigators directly through the heart generally leads to destructive interference between the pencil beam navigators and the imaging volume, affecting image quality and navigator accuracy.

SUMMARY OF THE DISCLOSURE

Navigator methods are disclosed that may be used to compensate for motion-induced distortions of magnetic resonance images. The navigator methods are based on detecting a flow sensitive signal within a volume of a subject to be imaged, and using the detected fluid motion as a reference point to track subject motion during data acquisition. In a disclosed embodiment, rapid blood flow in the left ventricle of the heart is detected, and used to prospectively track motion of the heart in three dimensions. Compensation for respiratory motion may also be provided.

Also disclosed are magnetic resonance systems for motion compensation using the disclosed navigator methods. Control over data acquisition and processing in the magnetic resonance systems may be provided by a computer readable medium storing the instructions for the disclosed methods.

DETAILED DESCRIPTION

Figure 1:
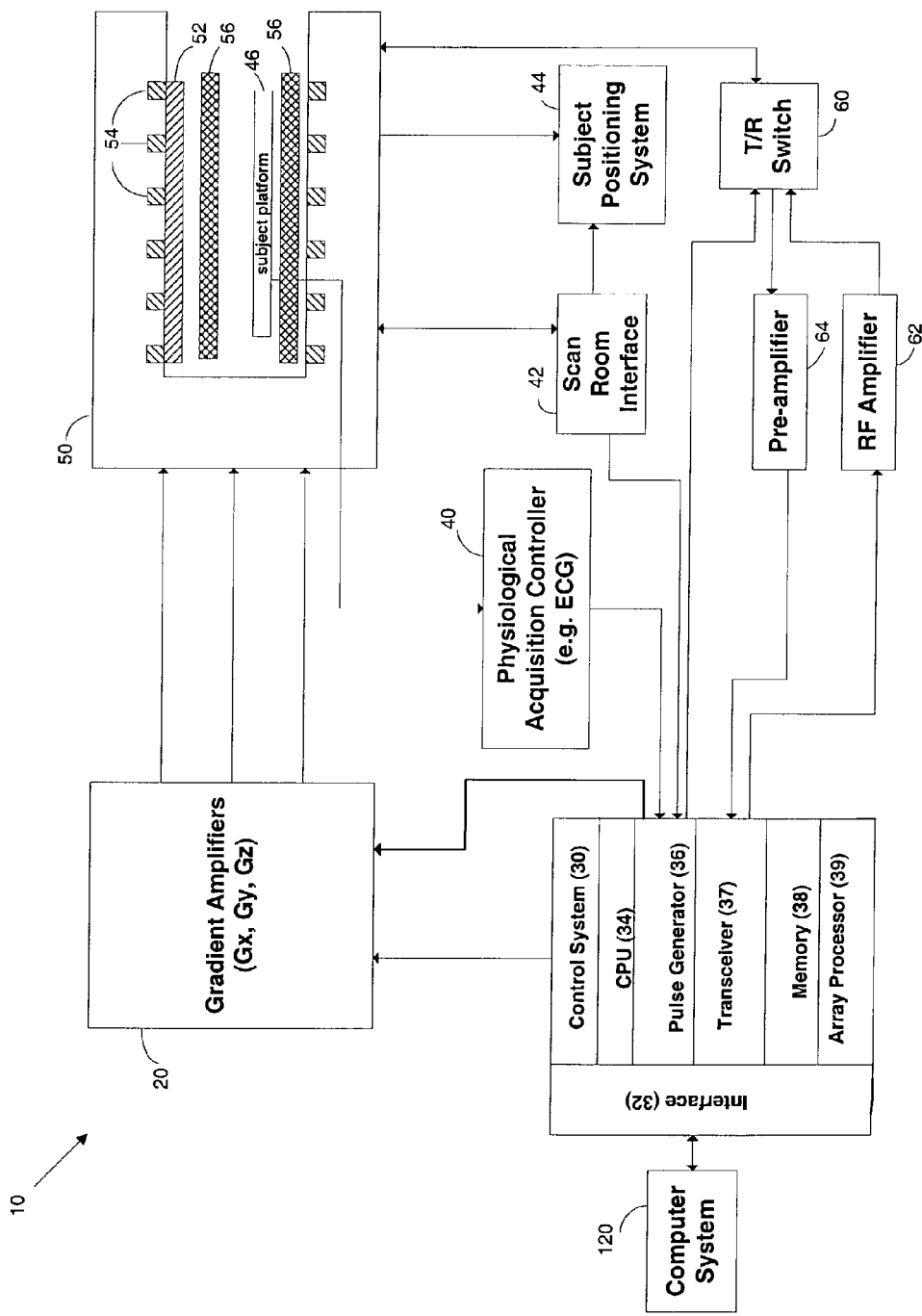
FIG. 1 is a diagram of a magnetic resonance imaging system that may be used to practice the disclosed methods.

In order to facilitate review of the various embodiments of the invention, the following explanations of specific abbreviations and terms are provided:

I. ABBREVIATIONS

SI—superior-inferior (head to toe).
AP—anterior-posterior (front to back).
LR—left-right.
LV—left ventricle.
RaMP—Rapid Motion Perception.
CD—complex difference.
TR/TE/α—repetition time/echo time/RF flip angle.
FLASH—Fast Low Angle Shot.
FISP—Fast Imaging with Steady Precession.
MR—magnetic resonance.
MRI—magnetic resonance imaging.
FFT—Fast Fourier Transform.
RF—radio-frequency electromagnetic radiation.

II. TERMS

Unless otherwise explained, all technical and scientific terms used herein have the same meaning as commonly understood by one of ordinary skill in the art to which this invention belongs. Definitions of common terms in Magnetic Resonance may be found, for example, in Haacke, "Magnetic resonance imaging: physical principles and sequence design," ISSN/ISBN 0471351288 and Vlaardingerbroek and den Boer, "Magnetic resonance imaging: theory and practice," ISSN/ISBN 3540648771.

The singular terms "a," "an," and "the" include plural referents unless context clearly indicates otherwise. Similarly, the word "or" is intended to include "and" unless the context clearly indicates otherwise. The word "comprises" means includes. Although methods, systems and materials similar or equivalent to those described herein can be used in the practice or testing of the present invention, suitable methods and materials are described below.

As used herein, the term "navigator" refers to an MRI echo used to provide a reference position that may be used to compensate for motion, for example, subject motion, such as respiratory motion, between imaging scans. Navigator echoes collected along a straight line in k-space are called linear navigators, whereas navigators collected in a circle centered at the origin of k-space are called circular or orbital navigators. Circular or orbital navigators are 2-D and 3-D variations from the basic one-dimensional magnetization selection. Circular navigators utilize RF pulses which can select ("excite") a two-dimensional zone, or slice, while orbital navigators utilize RF pulses which can select/excite a three-dimensional volume. A pencil beam navigator is an example of a circular navigator, obtained by applying a two-dimensional RF pulse. Linear, circular and orbital navigators may be used in the disclosed RaMP navigators. The term "k-space" refers to the mathematical space in which the Fourier transform of a spatial function is represented.

The term "flow encoded pulse sequence" refers to a sequence of MRI pulses that provide a "flow-sensitive signal." A flow-sensitive signal is proportional to the amount of fluid motion within a volume excited by the flow-sensitive pulse sequence. A flow sensitive signal may be used as a "flow-sensitive navigator." A flow sensitive navigator provides a reference position that corresponds to an area within a subject exhibiting fluid motion.

The term "subject" refers to any object, animate or inanimate, that is imaged using the disclosed MRI methods. More typically, however, a subject is a mammal, such as a human.

The term "volume" refers to any portion of a subject's body, but more particularly to a portion of a subject's body where blood flow is sufficient to provide a flow-sensitive MR signal.

All publications, patent applications, patents, and other references mentioned herein are incorporated by reference in their entirety. In case of conflict, the present specification, including explanations of terms, will control. In addition, the materials, methods, and examples are illustrative only and not intended to be limiting. Various embodiments are illustrated by the following non-limiting Examples.

III. EXAMPLES

The disclosed navigator methods represent a superior alternative to prior methods of compensating for motion in MR images, and are based in part on Rapid Motion Perception (RaMP). RaMP navigators are flow-sensitized navigator echoes, which utilize the movement of a blood volume as a marker for the position of a subject's body, or a particular organ or part of an organ, such as the heart or kidney. RaMP navigators may be utilized to simultaneously monitor motion in multiple directions. For example, RaMP navigators may be used to simultaneously monitor displacements in the superior-inferior (SI) and anterior-posterior (AP) directions. Unlike other prospective navigation schemes, there is no reliance on empirical correlations between the motions in different parts of a subject, thereby increasing reliability for individual patients. Also, RaMP navigators may utilize small flip angles ($\alpha \leqq 10°$) which diminishes interference with subsequent scans, while yielding adequate signal to noise ratios (SNR).

In a disclosed embodiment (see, Example 1 below), the ventricular blood volume was detected based on its high flow rate using a flow-encoded pulse sequence. The position of the blood volume was used as a direct representation of the position of the heart. The position of the heart may be detected prospectively, and used to successfully track bulk motion of the heart over the entire respiratory period, thereby providing improved image clarity and resolution.

In some embodiments, methods are provided for correcting a magnetic resonance image for subject motion during image acquisition. A volume within a subject is excited with a flow encoded pulse sequence, and a flow-sensitive signal associated with blood flow within the excited volume of the subject is detected. The position of the flow-sensitive signal may be used as a navigator for tracking subject motion between image acquisition events. In general, the flow-sensitive signal may be positioned anywhere that the change in position of a moving blood volume may be representative of the motion of an organ. For example, all the major blood vessels around the heart, in the extremities, and in the brain may be used to provide a navigator signal based on blood flow. In a particular embodiment, the volume within the subject that is excited includes at least a portion of the left ventricle of the heart. In other particular embodiments, the excited volume includes a blood vessel in the kidney or the coronary bed.

Another possible application of the RaMP approach is as a calibration check for diaphragm-based conventional navigators. As discussed in the background, diaphragm-based navigators need correlation coefficients for obtaining correct heart position from the diaphragm position, and the value of these coefficients can change during a scan. Combining RaMP navigators with these diaphragm-based navigators may allow measurement of these coefficients directly during a scan, and also allow for the cross-checking of their value at arbitrary time locations in a scan.

The flow-encoded pulse sequence may be directed along any directions that pass through a subject, and in particular may be directed through the LV in any direction. Desirably, the direction along which flow encoding is performed substantially coincides with the principal direction of fluid motion within the excited volume. In more particular embodiments, the flow-encoded pulse sequence is directed through the LV and in one or more of the SI, AP or LR directions. The timing of a flow-encoded pulse sequence used for exciting a flow-sensitive signal within the LV may be adjusted to coincide with either mid-systole or mid-diastole.

In one embodiment, the flow encoded pulse sequence comprises a bipolar velocity-encoding gradient. In more particular embodiments, the flow encoded pulse sequence comprises a FLASH sequence incorporating the bipolar velocity-encoding gradient. More generally, however, any pulse sequence that can be used to detect the motion of excited spins within a subject may be employed as the flow-encoded pulse sequence. There are at least two main approaches to flow imaging: Phase contrast (PC) [see, for example, P. R. Moran, "A Flow Velocity Zeugmatographic Interlace for NMR Imaging in Humans," Mag. Reson. Imaging., 1: 197-203 (1982) and Nayler et al., "Blood Flow Imaging by Cine Magnetic Resonance," J. Comput. Assist. Tomogr., 10:715-722 (1986)] and Complex Difference (CD) imaging [see, for example, Dumoulin and Hart, "Magnetic Resonance Angiography," Radiology; 161:717-720 (1986) and Polzin et al., "A Complex-Difference Phase-Contrast Technique for Measurement of Volume Flow Rates," J. Mag. Reson. Imaging; 5:129-137, (1995)], which are used to detect and quantify blood flow. Also, there have been several novel approaches developed to combine these techniques with SSFP (steady-state free precession) for flow imaging using fast imaging techniques [see, for example, Pai and Wen, "Optimization of Steady-State Pulse Sequences for Fast Phase Difference and Complex Difference Flow Imaging," In: Proceedings, ISMRM, $9^{th}$ annual meeting (2001); Overall et al., "Oscillating Dual-Equilibrium Steady State Angiography (ODESSA)," In: Proceedings, ISMRM, $9^{th}$ annual meeting (2001); and Overall et al., "Fast Motion Encoding using Steady State Echoes," In: Proceedings, ISMRM, $9^{th}$ annual meeting (2001)]. Flow-encoding pulse sequences include those that impart a velocity-dependent phase shift to the transverse magnetization of moving spins while leaving stationary spins unaffected. Examples of flow-encoded pulse sequences, and application thereof to detect fluid motion, may also be found, for example, in U.S. Pat. Nos. 5,093,620, 5,517,117, 6,141,578 and 6,377,831.

In a particular embodiment, the position of a flow sensitive signal within a subject is detected by calculating the complex difference between a transverse magnetization detected after a first bipolar velocity encoding gradient, and a transverse magnetization detected after a second bipolar gradient. The position of the flow-sensitive signal within a subject may be used to correct for subject motion before, during or after MRI image acquisition. In a particular embodiment, the position of the flow-sensitive signal within the volume is used to prospectively shift a position of a subsequent imaging slice to compensate for subject motion between a first imaging sequence of pulses and a second imaging sequence of pulses.

In another embodiment, methods are disclosed for correcting a magnetic resonance image of the heart for subject motion during image acquisition. These methods include exciting a region of a subject including at least a portion of the blood volume of the heart (e.g. a portion of the LV) with a flow-encoded pulse sequence, detecting a signal associated with blood flow within the heart, and using the position of the signal as a reference position for correcting the image of the heart for subject motion during image acquisition. In particular embodiments, flow-encoded pulse is timed to coincide with mid-systole or mid-diastole, and may be used to provide a prospective navigator signal that permits shifting of a subsequent image slice acquisition.

In yet other embodiments, prospective motion correction methods are provided. These methods include exciting a volume within a subject with a flow encoded pulse sequence, detecting a current flow-sensitive echo, calculating a current position of the current flow-sensitive echo relative to a reference position previously established for a reference flow-sensitive echo, and translating a subsequent imaging slice to compensate for a difference between the current and reference positions due to subject motion. In particular embodiments, the amount of compensation along the flow-encoding axis is determined by calculating a current position relative to a reference position for the flow-sensitive echo. A one-dimensional Fast Fourier transform may be performed on a complex difference calculated for the reference flow-sensitive echo to provide a reference spectrum. A one-dimensional Fast Fourier transform may also applied to the current flow-sensitive echo to provide a current spectrum. The current spectrum may then be multiplied by the mirror image of the reference spectrum to provide a product, and a Fast Fourier transform is applied to the product to provide a measure of the difference between the current and reference positions. This difference may then be applied to shift the image slice prospectively.

In another embodiment, a MRI system is provided. The system may include a magnet for producing a polarizing magnetic field, an RF system for exciting spins in a subject positioned in the polarizing field, a gradient system for producing magnetic field gradients in the subject, a pulse generator connected to the RF system and the gradient system to provide flow-encoded pulse sequences. Also included in the MRI system is computer system, the computer system including a computer readable medium having stored thereon the instructions for generating a flow-sensitive navigator signal and for shifting an imaging slice in response to a change in the position of the flow sensitive navigator. A computer-readable medium having the instructions for implementing any of the disclosed methods or variations thereof is also part of the disclosure.

Image acquisition in the disclosed methods may be performed using any known or later disclosed imaging sequence. Examples of imaging pulse sequences include, for example, SSFP (Steady-State Free Precession Imaging) [see, for example, Ernst and Anderson, "Application of Fourier Transform Spectroscopy to Magnetic Resonance," *Rev. Sci. Instr.*, 37(1): 93-102 (1966); Freeman and Hill, "Phase and Intensity Anomalies in Fourier Transform NMR," *J. Magn. Reson.*, 4:366-382 (1971); Hinshaw, "Image Formation by Nuclear Magnetic Resonance: the Sensitive-Point Method," *J. Appl. Phys.*, 47(8):3709-3721 (1976); and Hawkes and Patz., "Rapid Fourier Imaging using Steady-state Free Precession," *Magn. Reson. Med.*, 4:9 (1987)], EPI (Echo-Planar Imaging) [see, for example, Mansfield, "Multiplanar Image Formation using NMR spin echoes," *J. Phys. C: Solid State Phys.*, 10:L55 (1977), and Mansfield and Pykett, "Biological and Medical Imaging by NMR," *J. Magn. Reson.*, 29:355-373 (1978)]; GRE (Gradient Recalled Echo) [see, for example, van der Meulen et al., "Very Fast MR Imaging by Field Echoes and Small Angle Excitation," *Magn. Res. Im.* 3:297-299 (1985), and Haase et al., "Rapid Imaging and MR Movies," *SMRM Book of Abstracts* 980-981 (1985)], SE (Spin-Echo) [see, for example, Hahn, "Spin Echoes," *Phys. Rev.* 80:580 (1950)], StE (Stimulated Echo) [see, for example, Frahm et al., "Stimulated Echo Imaging," *J Magn Reson* 64(1):81-93 (1985), and P. T. Callaghan, "Principles of nuclear magnetic resonance microscopy," Oxford: Clarendon Press, p. 430 (1991)], and their derivatives such as FLASH [see, for example, Haase et al., "FLASH Imaging: Rapid NMR imaging using low flip-angle pulses," *J. Magn. Reson.*, 67:258-266 (1986)], FISP [see, for example, Oppelt et al., "FISP: A new fast MRI sequence," *Electromedica*, 54:15-18 (1986)], Black-blood imaging [see, for example, Edelman et al., "Fast Selective Black Blood MR Imaging," *Radiology*, 181:655-660 (1991)], Chemical Shift Imaging [Haase et al., "1H NMR Chemical Shift Imaging," *Phys. Med. Biology*, 30(4):341-344 (1985)], Inversion Recovery Imaging [Vold et al., "Measurement of Spin Relaxation in Complex Systems," *J. Chem. Phys.* 48:3831-3832 (1968)], among others. The imaging sequences can be applied as a single-shot technique or with segmentation of k-space, and can also be used to optimize the utilization of the sequences with the RaMP technique. If the imaging technique saturates the magnetization over a cardiac cycle, then a delay of several cardiac cycles may need to be imposed before reapplying the RaMP navigators and the imaging sequence, in order to allow the longitudinal magnetization to recover.

Example 1

MRI System

An exemplary MRI system is illustrated in FIG. 1. Referring to FIG. 1, the major components of a MRI system 10 that may be used to practice the disclosed methods are shown. The operation of the system is controlled by computer system 120 (see, Example 4 below). The computer system 120 includes a number of modules that communicate with each other, and with control system 30, through interface 32.

The control system 30 includes a set of modules connected together by an interface 32, and also connected to computer system 120 through interface 32. These modules include a CPU module 34. A pulse generator module 36 operates the system components to carry out the desired scan sequence and produces data which indicates the timing, strength and shape of the RF pulses produced, and the timing and length of the data acquisition window. The pulse generator module 36 connects to a set of gradient amplifiers 20, to indicate the timing and shape of the gradient pulses that are produced during the scan. The pulse generator module 36 also receives subject data from a physiological acquisition controller 40 that receives a signal from one or more sensors connected to the subject, such as an ECG signal from electrodes attached to the subject. The pulse generator module 36 also connects to a scan room interface circuit 42 that receives signals from various sensors associated with the condition of the patient and the magnet system. It is also through the scan room interface circuit 42 that a subject positioning system 44 receives commands to move the subject on subject platform 46 to the desired position for the scan.

The gradient waveforms produced by the pulse generator module 36 are applied to the gradient amplifier system 20 having Gx, Gy, and Gz amplifiers. Each gradient amplifier excites a corresponding gradient coil in an assembly designated 52. The gradient coil assembly 52 forms part of a magnet assembly 50 which includes a polarizing magnet 54 and a whole-body RF coil 56. A transceiver module 37 in the control system 30 produces pulses that are amplified by a RF amplifier 62 and coupled to the RF coil 56 by a transmit/receive switch 60. The resulting signals radiated by the excited nuclei in the patient may be sensed by the same RF coil 56 and coupled through the transmit/receive switch 60 to a preamplifier 64. The amplified NMR signals are demodulated, filtered, and digitized in the receiver section of the transceiver 37. The transmit/receive switch 60 is controlled by a signal from the pulse generator module 36 to electrically connect the RF amplifier 62 to the coil 56 during the transmit mode and to connect the preamplifier 64 during the receive mode. The transmit/receive switch 60 also enables a separate RF coil (for example, a surface coil) to be used in either the transmit or receive mode.

The following is a brief description of the acquisition and storage of MR data. The NMR signals picked up by the RF coil 56 are digitized by the transceiver module 37 and transferred to a memory module 38 in the system control 32. When a scan is completed, an array of raw k-space data has been acquired in the memory module 38. This raw k-space data is rearranged into separate k-space data arrays for each image to be reconstructed, and each of these is input to an array processor 39 which operates to Fourier transform the data into an array of image data. This image data is conveyed through interface 32 to the computer system 120, where it may be stored and/or processed according to the disclosed methods.

Example 2

Cardiac Navigator

In this example, a cardiac navigator approach is described. The fast-flowing blood volume in the heart is tracked during the cardiac cycle. Due to its sensitivity to high velocity blood flow, the approach may be referred to as a Rapid-Motion-Perception (RaMP) navigator. In this approach, performing a complex difference analysis of the flow-sensitized profiles isolates the fast moving blood volume in the ventricles during the systolic emptying (or diastolic filling). The complex difference analysis suppresses the stationary or slow-moving spins in the excited volume. Simultaneous tracking of superior-inferior (SI) and anterior posterior (AP) movement of the heart is demonstrated by this approach. Small flip angle excitations gave sufficient SNR without creating saturation effects.

Figure 2:
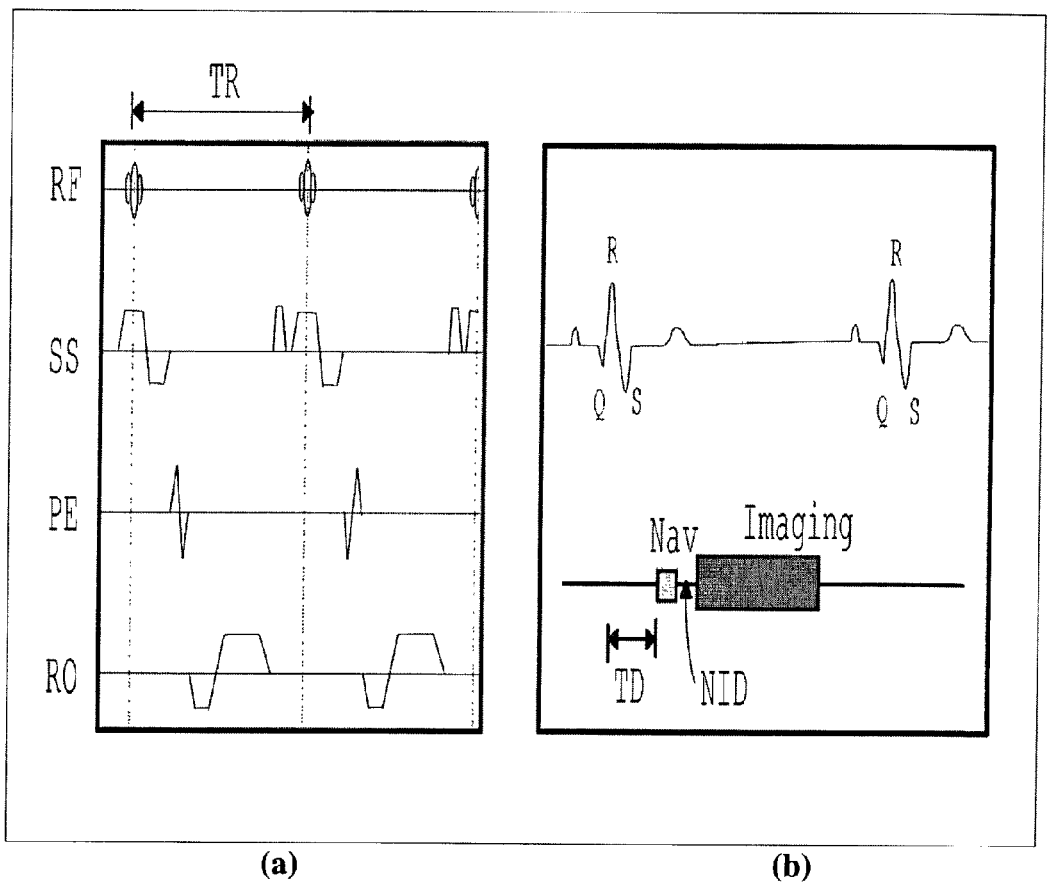
FIG. 2 is a diagram showing the pulse and timing sequences for a particularly disclosed flow-sensitive navigator (RaMP) scheme.

FIG. 2 shows a particular embodiment of the flow-sensitive navigator (RaMP) pulse scheme. In this instance, the RaMP sequence is comprised of a spoiled-Fast Low Angle Shot (FLASH) sequence that incorporates alternating bipolar velocity-encoding gradients (see, for example, Haase et al., "FLASH Imaging: Rapid imaging using low flip-angle pulses," *J. Magn. Reson.*, 212: 579-587 (1986) and Crawley and Henkelman, "Errors in T2 estimation using multislice multiple-echo imaging," *Magn. Res. Imaging.*, 67: 258-266 (1987)). A particular timing and shape of the pulse sequence is shown in FIG. 2(*a*), where TR represents the repetition time between successive applications of RF pulses, PE represents the phase-encode direction along which velocity encoding is performed, SS represents the slice-select direction and RO is the readout-direction. FIG. 2(*b*) shows a relative timing of the RaMP (Nav) sequence and the imaging sequence, where NID is the Navigator-Imaging Delay time and TD is the trigger delay. TD is the period between an electrocardiographic (ECG) trigger pulse (in this case, the R wave of the ECG trace shown at top) and a period of optimal blood flow within the left ventricular blood volume (in this case, mid-systole).

The alternating pair of bipolar velocity encoding gradients incorporated in the RaMP navigator pulses provides a signal that may be used to localize the fast moving blood volume within the LV. If $M_{1,k}$ and $M_{2,k}$ represent the transverse magnetization in the readout direction after the first and second bipolar gradients, respectively, for the $k^{th}$ navigator echo, then the complex difference for the RaMP scheme (CD) is given by $$CD = |M_{2,k} - M_{1,k}| \quad [1]$$

where the transverse magnetization values are obtained by performing a one-dimensional Fourier Transform (FT) on the raw data along the readout, or frequency-encoding, direction.

The first cardiac cycle scan may be used as the reference scan, and establishes the reference position of the heart, i.e., the CD profile of the blood volume for this cycle is used as the reference profile. This reference profile is then used as a marker, and compared with the CD data of subsequent scans to determine their offsets from the reference position. Mathematically, this comparison is realized with standard motion analysis by profile correlation, detailed below.

A reference profile is obtained by first applying a one-dimensional Fast-Fourier Transform (FFT) on the complex difference data for the reference scan, before applying a Fermi filter. A Fermi filter is a bandpass filter that only accepts a signal within a certain frequency range, or band. The Fermi filter may be used for suppressing artifacts due to the finite window of acquisition in the k-space, and for reducing the noise level of the RaMP echoes. The filtered spectral data may then be zero-filled, after which a one-dimensional inverse (FFT) is performed. Finally, values below an arbitrary amplitude threshold were eliminated to minimize the influence of noise, and to provide the one-dimensional reference profile.

For profile correlation of the CD data of the subsequent scans with the reference scan, one-dimensional FFT is applied to subsequent CD data, and the spectral data are zero-filled and multiplied with the spectrum of a mirror image of the reference profile. Application of a FFT operation to this product yields the sliding correlation between the profiles, which can then be used to determine the position shift in subsequent scans (see, for example, Ehman and Flemlee, "Adaptive technique for high-definition MR imaging of moving structures," *Radiology*, 173: 255-263 (1989)).

As mentioned above, FIG. 2(*b*) shows an illustrative timing sequence for RaMP guided imaging. The sequence is electrocardiographically gated (ECG-gated), and a trigger delay (TD) is used to locate the RaMP in mid-systole (or mid-diastole) to obtain the maximum flow signal. The RaMP data may be analyzed in real-time and the position corresponding to the motion of the heart computed during the time delay between the navigators and the imaging sequence (navigator-imaging delay, NID). Typical numerical values for all the delay times are given below. The slice shift corresponding to the position change of the heart is applied during the NID and the imaging scan is then performed.

All the RaMP navigator-guided imaging scans were performed on a Siemens Sonata 1.5-T whole-body clinical scanner (Siemens Medical Systems (SMS), Erlangen, Germany), with a gradient set of 40 mT/m and maximum slew rates of 200 mT/m-ms. As mentioned earlier, the navigators were ECG-triggered, spoiled-FLASH echoes with the gradient spoiling in the Slice-Select direction, and including alternating pairs of bipolar velocity encoding gradients. For a given pair of RaMP echoes, each half (comprising of one bipolar encoding gradient) was implemented with a repetition time (TR) of 8 ms and an echo time (TE) of 3.5 ms, RF flip angle ($\alpha$) of 10° and slice thickness of 20 mm. The RaMP echoes occupy approximately 16 ms during a cardiac cycle, and may be performed along multiple axes simultaneously. For example, navigator information may be obtained simultaneously for the SI, AP and LR directions.

The imaging sequence following the navigator sequence in this embodiment was a single-shot Fast Imaging with Steady Precession (FISP) sequence that had a TR/$\alpha$ of 3.4/1.7/15°, and slice thickness of 8 mm. The image matrix was 128 pixels×64 pixels, while that of the navigator echoes was 128 pixels in the readout direction. The readout field-of-view (FoV) ranged between 260 and 395 mm, implying a linear resolution of 2.03-3.09 mm/pixel for the navigator echoes.

An ECG-prospectively triggered FLASH single-slice, multiphase breath-hold cine sequence (cine TurboFLASH; Siemens Medical Systems) with a TR/TE/$\alpha$ of 27/3.4/20° was used to determine the time to mid-systole for each human volunteer who participated in the navigator study. This time was used to determine the trigger delay time for the RaMP echoes. Typically, the TD time was 150 ms±20 ms, while the navigator-imaging delay (NID) was 2 ms.

Four normal volunteers (age 24-38 years) were scanned with a phased array surface coil using the following protocol:
  a. ECG-gated FLASH multi-slice multi-axis non-breath-hold localizers (TurboFLASH; SMS) were used to localize the heart,
  b. 3-D local volume-of-interest field shims were calculated with a manufacturer-supplied shimming sequence,
  c. the approximate time to mid-systole was determined by applying the cine sequence indicated above, and
  d. RaMP echoes were applied, followed by the imaging sequence, under free breathing and breath-hold conditions.

Steps a through c were performed only at the start of the experiment to set up the parameters for the execution of the final step, but may be repeated during extended imaging of a subject.

Heart motion tracked by the imaging sequence was compared to the motion predicted by the RaMP scheme to determine the reliability of the navigators. Motion detected in the images obtained from the imaging sequence, was reference on the position in the first cardiac cycle. Imaging scans for subsequent cardiac cycles were correlated to this reference image with a standard motion registration algorithm [see, for example, Ehman and Felmlee, "Adaptive technique for high-definition MR imaging of moving structures," *Radiology* 173: 255-263 (1989)].

Figure 3:
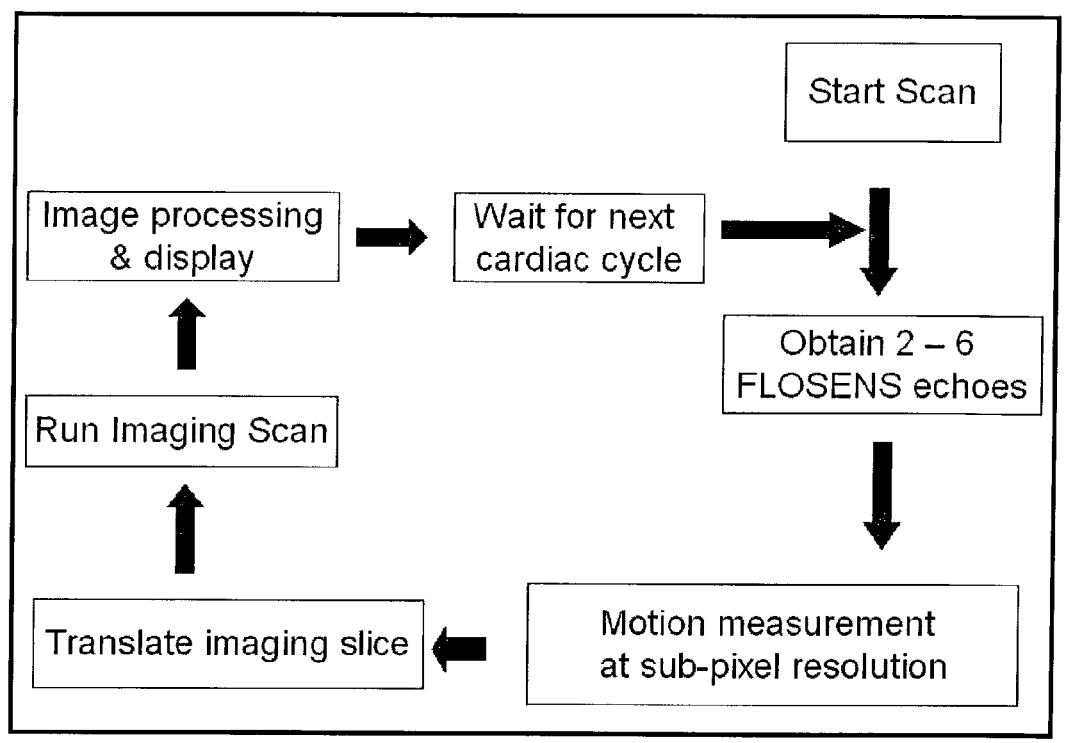
FIG. 3 is a block diagram illustrating a particular disclosed method for prospectively applying a RaMP scheme to compensate for patient motion during MR image acquisition.

Prospective application of RaMP navigation on the scanner was performed as shown in FIG. 3. Between 2 and 6 RaMP echoes were acquired, depending upon whether navigation in one dimension (2 RaMP echoes), two dimensions (4 RaMP echoes) or three dimensions (6 RaMP echoes) was performed. The navigator projection data was processed in real-time using a site-developed reconstruction package (utilizing the algorithm detailed above), and the displacement information obtained was used to translate the imaging slice before running the imaging sequence. For the two prospectively corrected cases (Case I and Case II, corresponding to two different human subjects) presented in this Example, a 2D version of RaMP was implemented, i.e. motion correction was applied only in the SI and AP directions, with flow encoding in the LR direction. In principle, flow encoding may be done in any direction with respect to a subject's body, an organ or the MRI system. Both the navigating and the imaging slices were, in this embodiment, sagittal in orientation. For Case I, an agarose-filled tube was placed above the phased-array surface coil to track the motion shift predicted by the navigator echoes, and the body coil was used as the receiver. For Case II, the phased-array surface coil was used as the receiver.

The superior-inferior (SI) motion dominates cardiac movement in the thorax. Anterior-posterior motion is only a fraction of the magnitude for SI motion, and typically the left right motion of the heart is negligible. LR motion was ignored in this example. RaMP navigators, in principle, may be used to track all three directions of cardiac motion, and prospectively slice shift in response to all movement in any or all of the three directions.

To verify the capability of the RaMP navigators to predict the cardiac displacement, and to determine the resolution range, a comparison was made of the displacements predicted by the RaMP navigators in the SI and AP directions, and those determined from the images obtained within the imaging sequence, under a non-prospective implementation. Bland-Altman plots were used to determine the 95% limits of agreement (estimated by mean difference ±1.96 standard deviation of the differences) between the measurements by the two approaches (see, for example, Bland and Altman, "Statistical Methods for Assessing Agreement between Two Methods of Clinical Measurement," *The Lancet*, 8: 307-310 (1986) and Bland and Altman, "Measuring Agreement in Method Comparison Studies," *Stat. Met. Med. Res.*, 8: 135-160 (1999).

Figure 4:
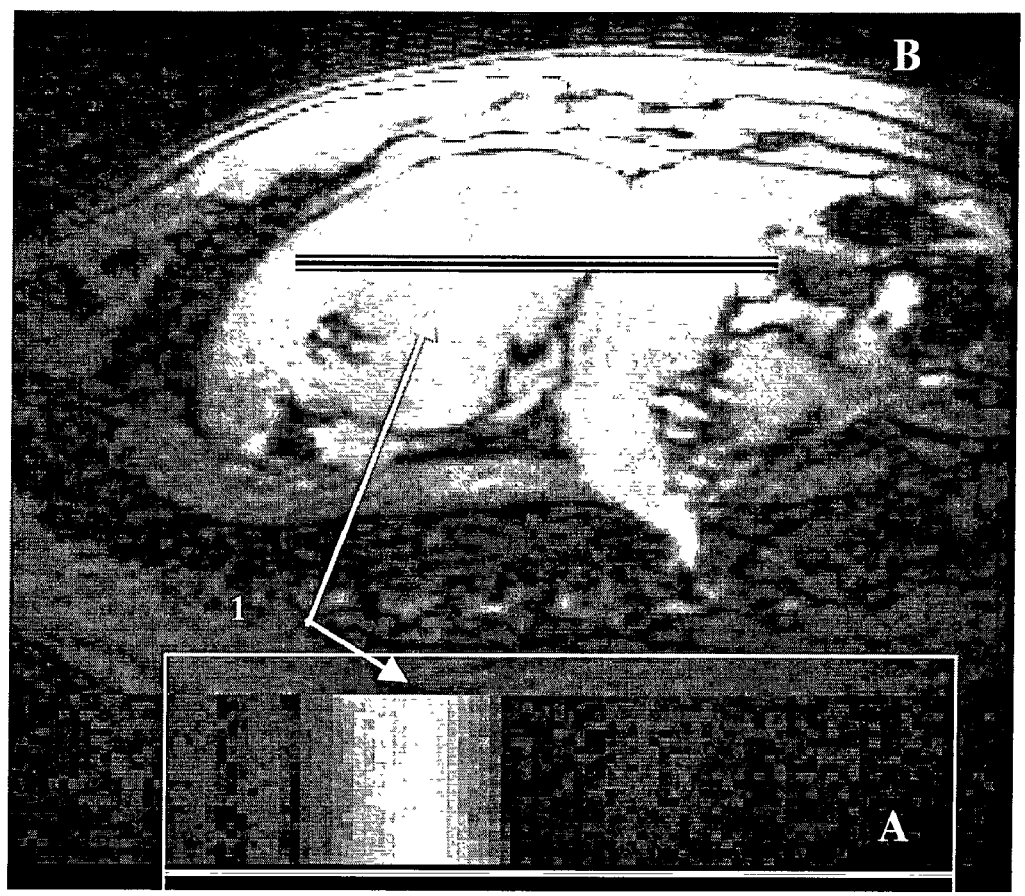
FIG. 4 is an image showing the position and intensity of a RaMP navigator echo over the course of a breath-hold scan (A) where flow encoding is performed in the LR direction. A sample MRI image (B) obtained during the scan using a FISP imaging sequence is also shown. Marker lines (indicated by 1) show the position of the heart, both in the FISP image and the navigator echoes.

Shown in FIG. 4A is the superior-Inferior (SI) cardiac position as indicated by a RaMP navigator during a breath-hold scan. From bottom to top, the location of the RaMP (flow-sensitive) signal during successive scans is shown in the horizontal bands. The most intense portion of the band is the position of the highest velocity blood volume within the LV. The navigator echoes in FIG. 4A clearly show that even under breath-hold conditions, a gentle drift in the heart position from head to foot is visible over the scan duration, due to the relaxation of the diaphragm over the breath-holding duration. FIG. 4B shows a sample image taken during the sequence. In both FIG. 4A and FIG. 4B, the arrows labeled as 1 indicate the location of the heart. The marker lines and arrows locate the navigator echoes relative to the diaphragm and the heart.

Figure 5:
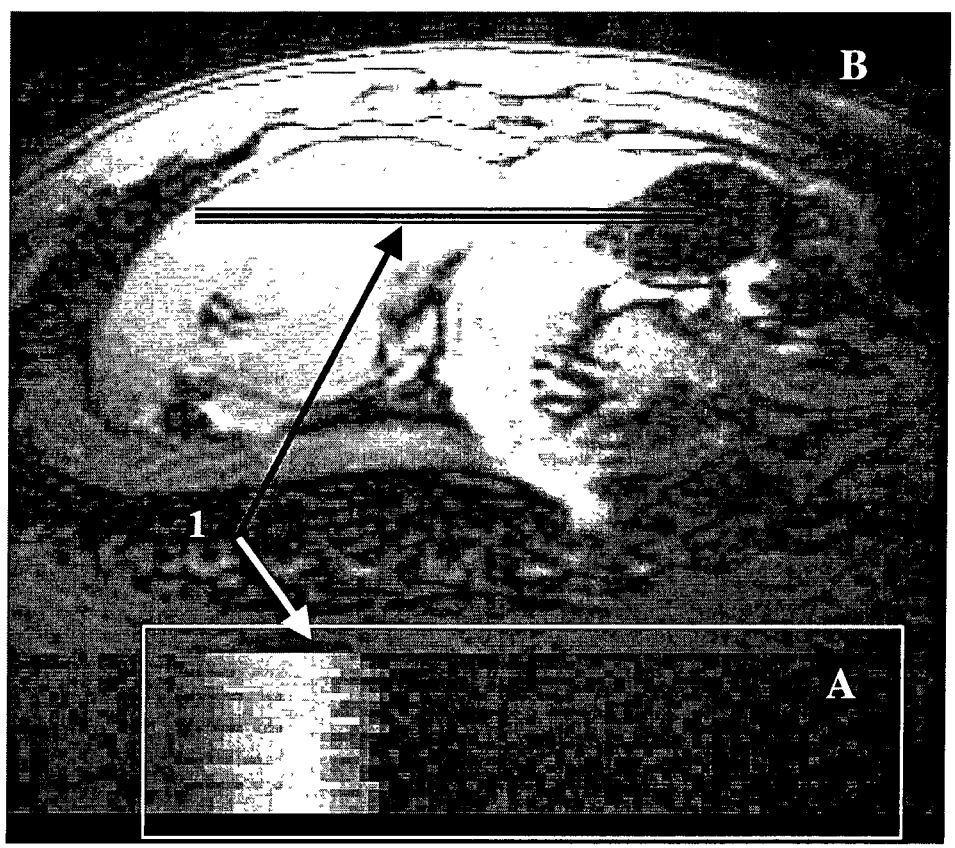
FIG. 5 is an image showing the position and intensity of a RaMP navigator echo over the course of a free breathing scan (A). A sample MRI image (B) obtained during the scan using a FISP imaging sequence is also shown. Marker lines (indicated by 1) show the position of the heart, both in the FISP image and the navigator echoes.

FIG. 5 shows the SI cardiac position as indicated by a RaMP navigator during a free breathing scan. As in FIG. 4, the position of the heart was followed using navigator echoes based on LR flow encoding. The arrows labeled with a 1 indicate the location of the heart. The variation in the grayscale values of the navigator echoes (FIG. 5A) over several scans that encompass several respiratory cycles clearly shows the cyclic motion of the heart from head to toe (SI) and back. FIG. 5B shows a sample image obtained using the FISP imaging sequence. The marker lines and arrows locate the navigator echoes relative to the diaphragm and the heart.

In both the breath-hold and free-breathing cases, the RaMP navigator echoes track cardiac position by tracking the blood volume in the heart. The RaMP signal is dominated by the ventricular blood volume and also contains the descending aorta to a lesser degree. The signal from the aorta is to the left of the LV signal, in the lower portion of the figure.

Figure 6:
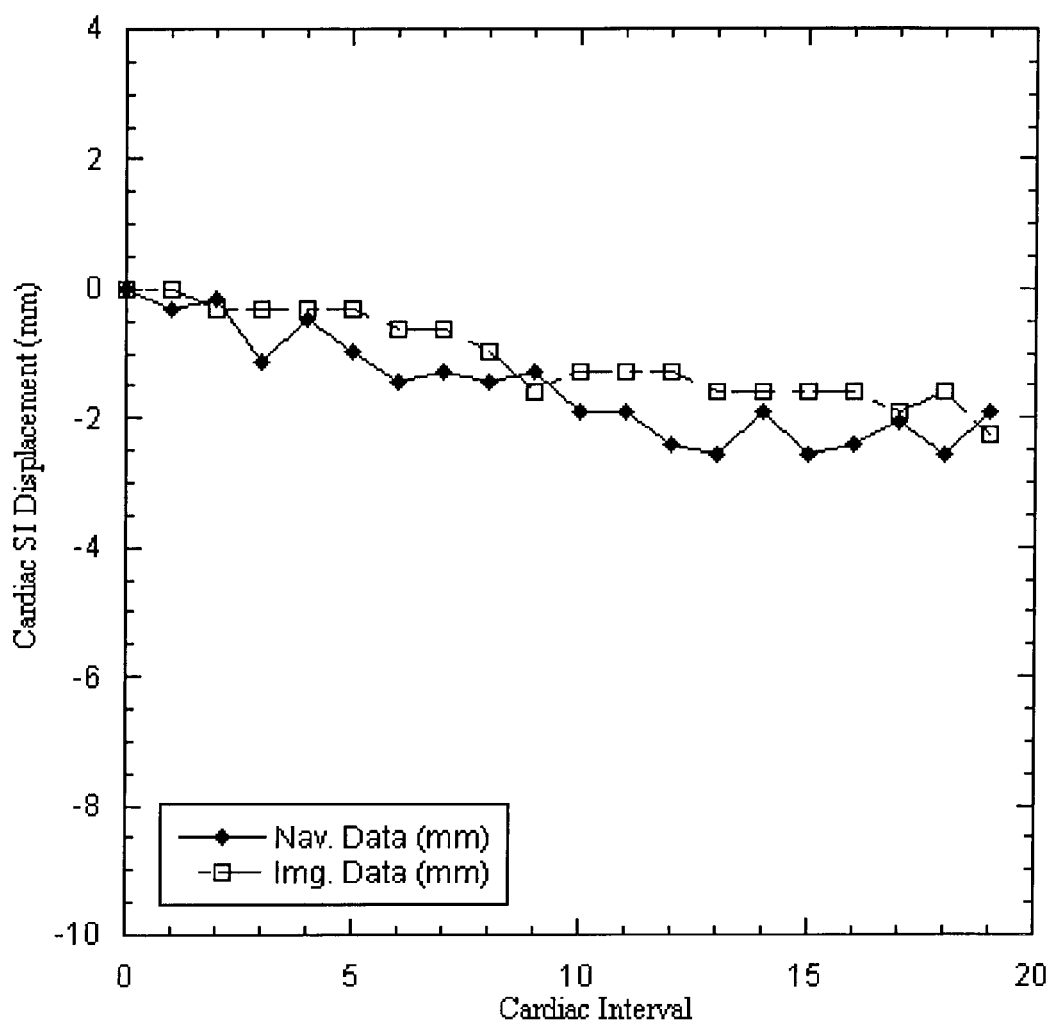
FIG. 6 is a plot of the SI displacement of the heart position for a breath-hold condition, as predicted by the RaMP navigators (diamonds), and as calculated from the imaging sequence (squares).
Figure 7:
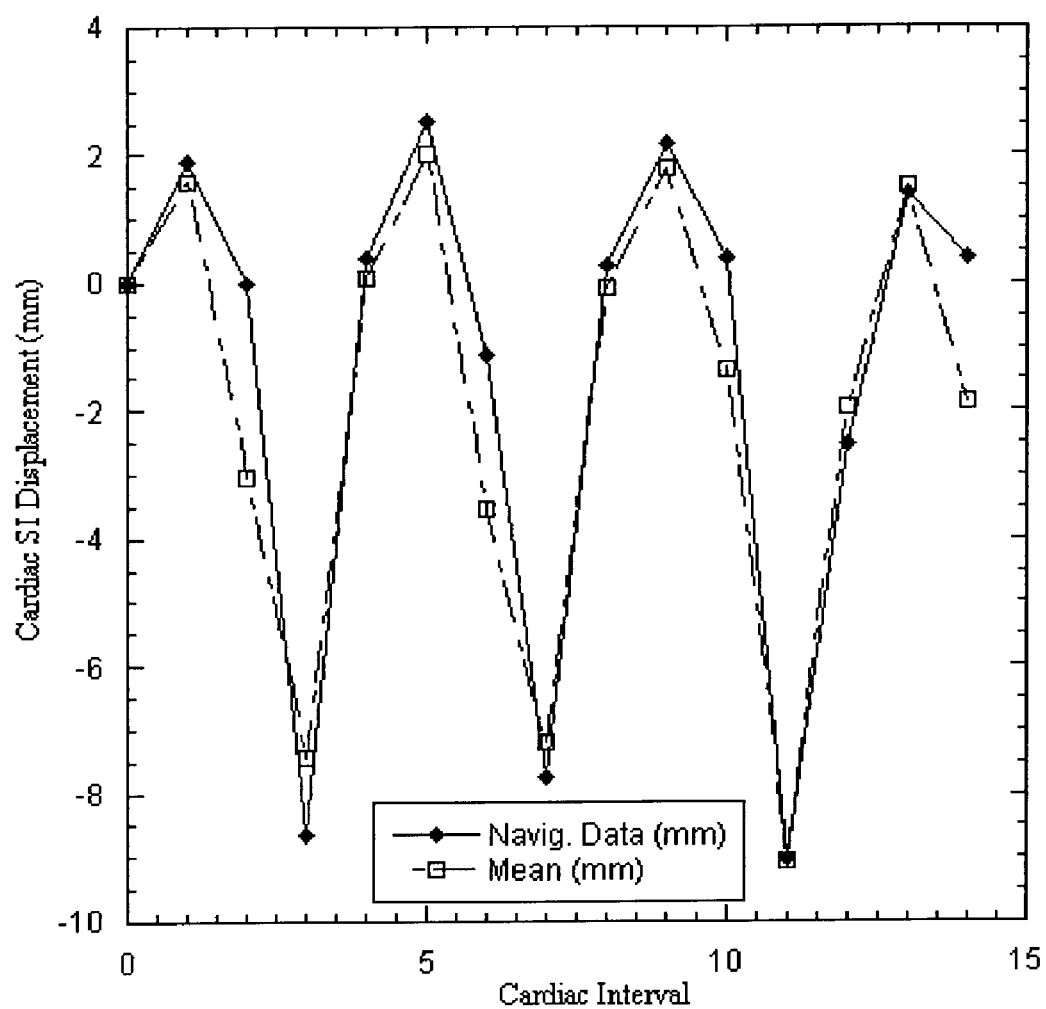
FIG. 7 is a plot of the SI displacement of the heart position for a free breathing condition, as predicted by the RaMP navigators, and as calculated from the images obtained through the imaging sequence.

A comparison of the heart displacement tracked using the RaMP navigator and the heart displacement determined from the images obtained during the imaging sequence was made for both the breath-hold and free-breathing cases discussed above. FIG. 6 shows the SI displacement of the heart position for a breath-hold condition as predicted by the RaMP navigators (w/LR flow encoding), and the displacement calculated from the imaging sequence. FIG. 7 shows the SI displacement of the heart position for a free breathing condition, as predicted by the RaMP navigators (w/LR flow encoding), and the displacement calculated from the images obtained through the imaging sequence.

In the breath-hold case (FIG. 6), the RaMP navigators predict a gentle drift in the position of the heart over the scan duration. There is good correlation between the heart motion predicted by the navigation scheme, and that obtained from the imaging sequence. The heart position is found to drift by approximately 2 mm during the scan duration. For the free breathing case (FIG. 7), the RaMP navigators and the images also provide good correlation between the motion predicted and the motion observed. The oscillatory nature of the motion observed corresponds to the grayscale variations noted in the RaMP CD navigators shown in FIG. 5a. In this scan, the heart moves approximately 11 mm in the SI direction during the scan.

Figure 8:
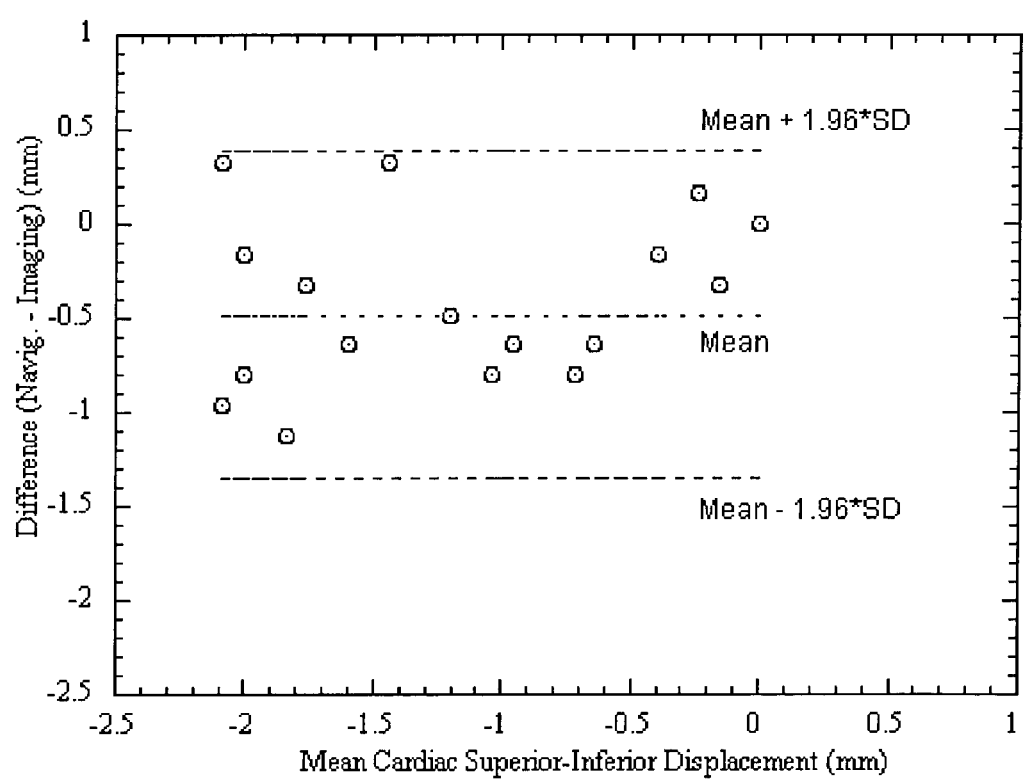
FIG. 8 is a Bland-Altman plot comparing the SI displacement for a breath-hold condition predicted by the RaMP navigators, and calculated from the images obtained through the imaging sequence.

FIG. 8 shows a Bland-Altman plot for the SI displacement for a breath-hold condition, as predicted by the RaMP navigators, and as calculated from the images obtained through the imaging sequence. There is a bias (less than 1 standard deviation (SD)) of the imaging measurements as compared to the navigator measurements. In this case, the bias is −0.48 mm, while the lower and upper 95% acceptance bounds are −1.344 mm and 0.384 mm respectively.

Figure 9:
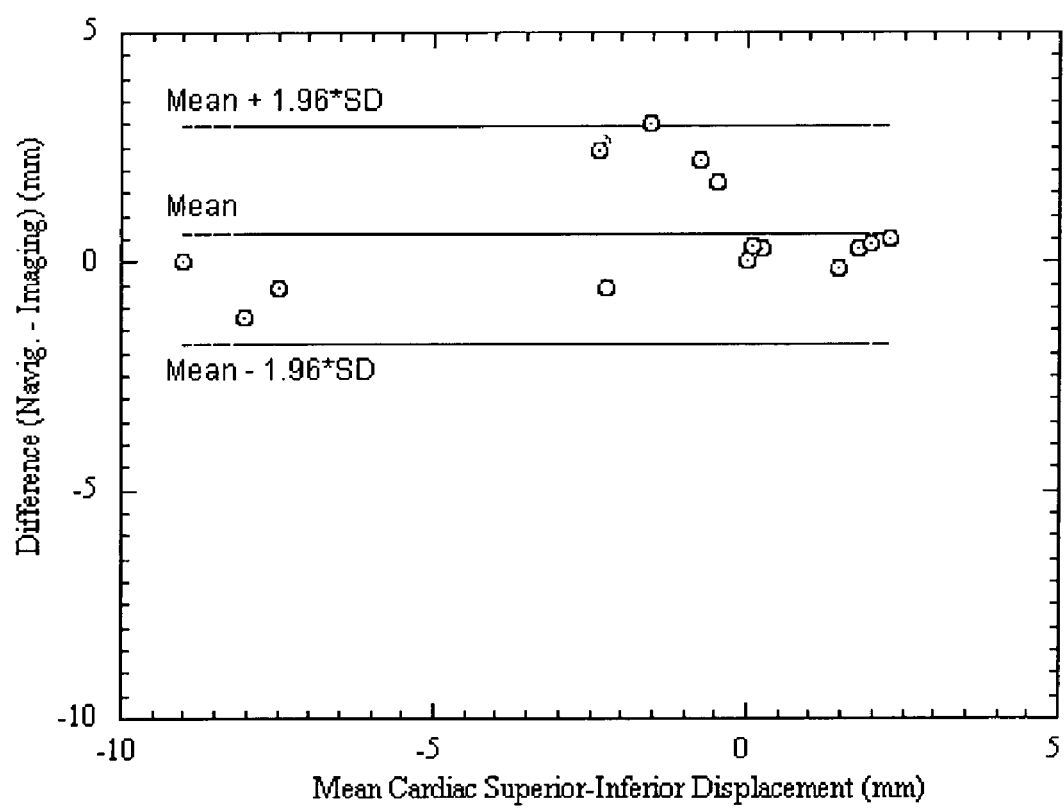
FIG. 9 is a Bland-Altman plot comparing the SI displacement for a free breathing condition, as predicted by the RaMP navigators, and calculated from the images obtained through the imaging sequence.

FIG. 9 shows a Bland-Altman plot for the SI displacement for a free breathing condition, as predicted by the RaMP navigators, and as calculated from the images obtained through the imaging sequence. There is a small bias of the navigator measurements as compared to the imaging measurements. In this case, the bias is 0.59 mm, while the lower and upper 95% acceptance bounds are −1.79 mm and 2.97 mm respectively. The one data point on the outskirts of the upper bound is within the 95% confidence interval (±1.16) of the upper bound.

Figure 10:
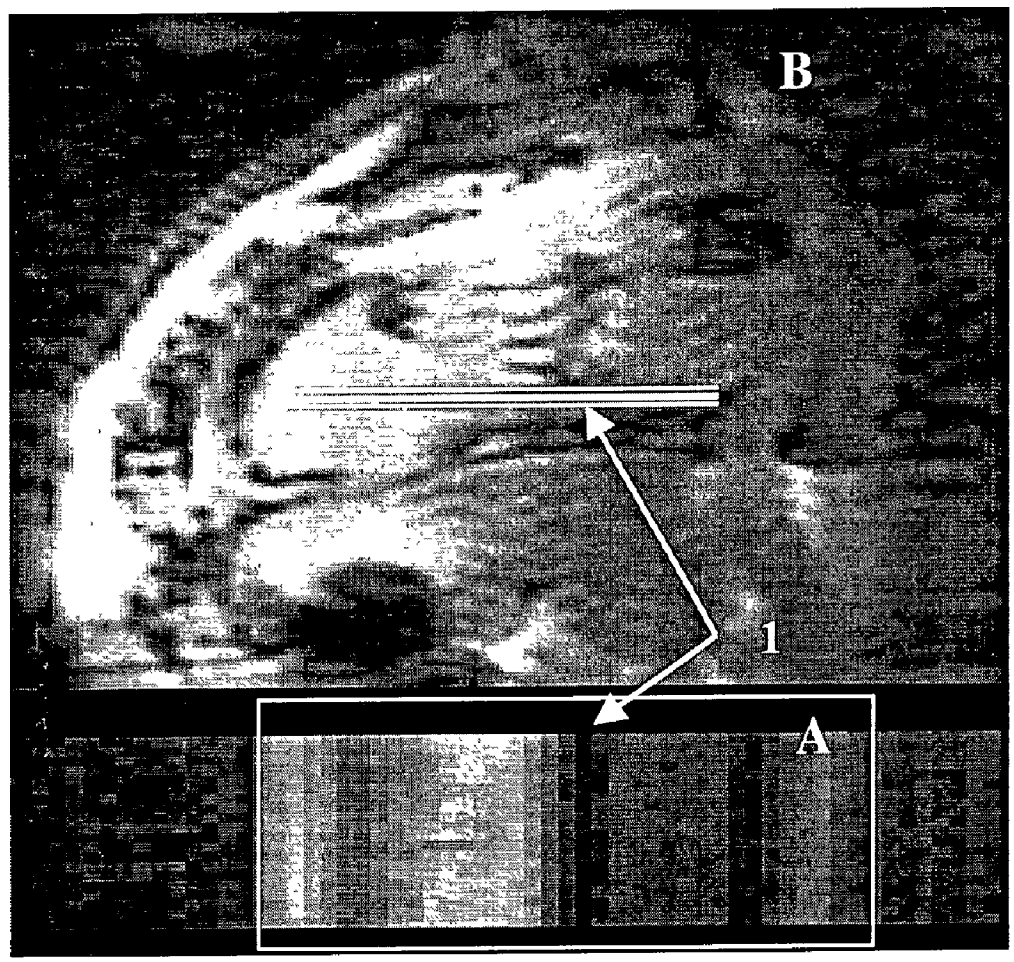
FIG. 10 is an image showing the AP cardiac position (A) as indicated by RaMP during a breath-hold scan with SI flow encoding. The arrows labeled as 1 indicate the location of the heart position. A sample image (B) obtained using the FISP imaging sequence is also shown. The marker lines and arrows locate the navigator echoes relative to the chest wall and the heart.
Figure 11:
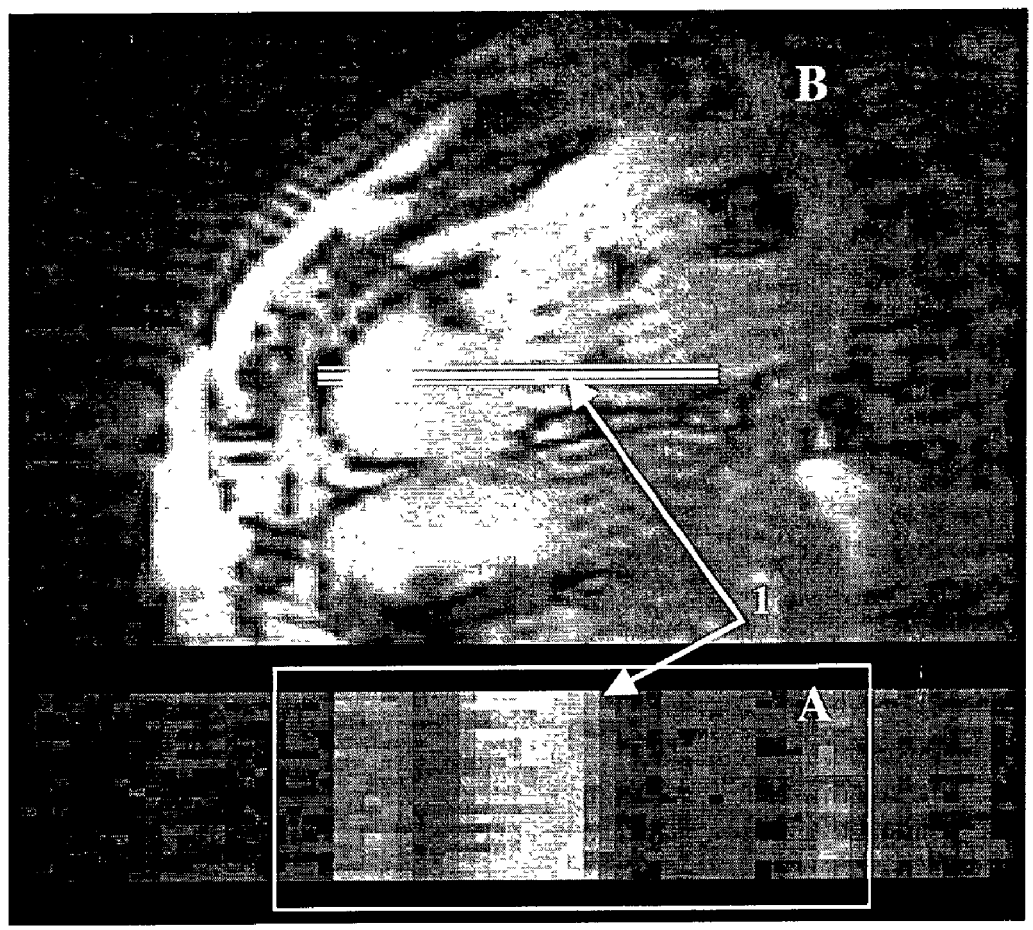
FIG. 11 is an image showing the AP cardiac position (A) as indicated by a RaMP navigator during a free breathing scan with LR flow encoding. The arrows labeled as 1 indicate the location of the heart position. A sample image (B) obtained using the FISP imaging sequence is also shown. The marker lines and arrows locate the navigator echoes relative to the chest wall and the heart.

The RaMP navigator methods were also applied to track Anterior-Posterior (AP) cardiac position breath-hold and free-breathing scans, using superior-inferior (SI) flow encoding. The RaMP CD navigators for the anterior-posterior (AP) motion of the heart are displayed in FIG. 10 and FIG. 11 for breath-hold and free breathing conditions respectively. An arrow labeled as 1 again indicates the location of the heart position in these figures.

As mentioned earlier, the heart moves considerably less in the AP direction than in the SI direction. Due to this, the signal contribution in the AP direction for the navigators will be substantially less than that for the SI direction. This may be discerned by comparing the signal intensity shown in FIG. 10A and FIG. 11A to the signal intensity in FIG. 4A and FIG. 5A. Nonetheless, the essential features of the heart motion in the AP direction can be determined from FIG. 10A and FIG. 11A. The RaMP navigators for the breath-hold case show that, unlike the SI direction, there is minor variation in the signal intensity in the AP direction over the scan duration. On the other hand, the navigators for the free breathing case reveal grayscale variations (note oscillation of the most intense signals from left to right), similar to that observed for the SI navigators, indicating that the heart motion in the AP direction is oscillatory over the respiratory cycle.

Figure 12:
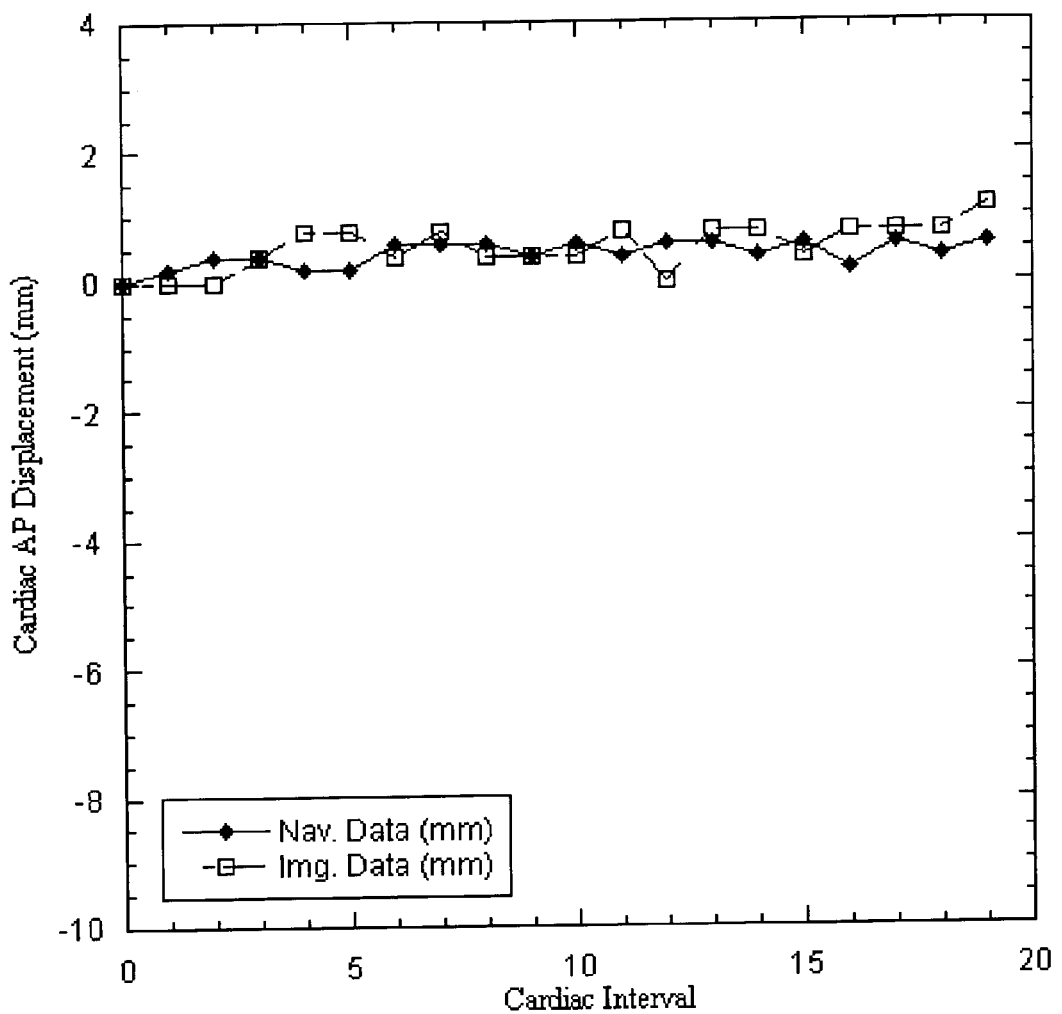
FIG. 12 is a plot of the AP displacement of the heart position for a breath-hold condition as predicted by the RaMP navigators (SI flow encoding), and as calculated from the images obtained through the imaging sequence.
Figure 13:
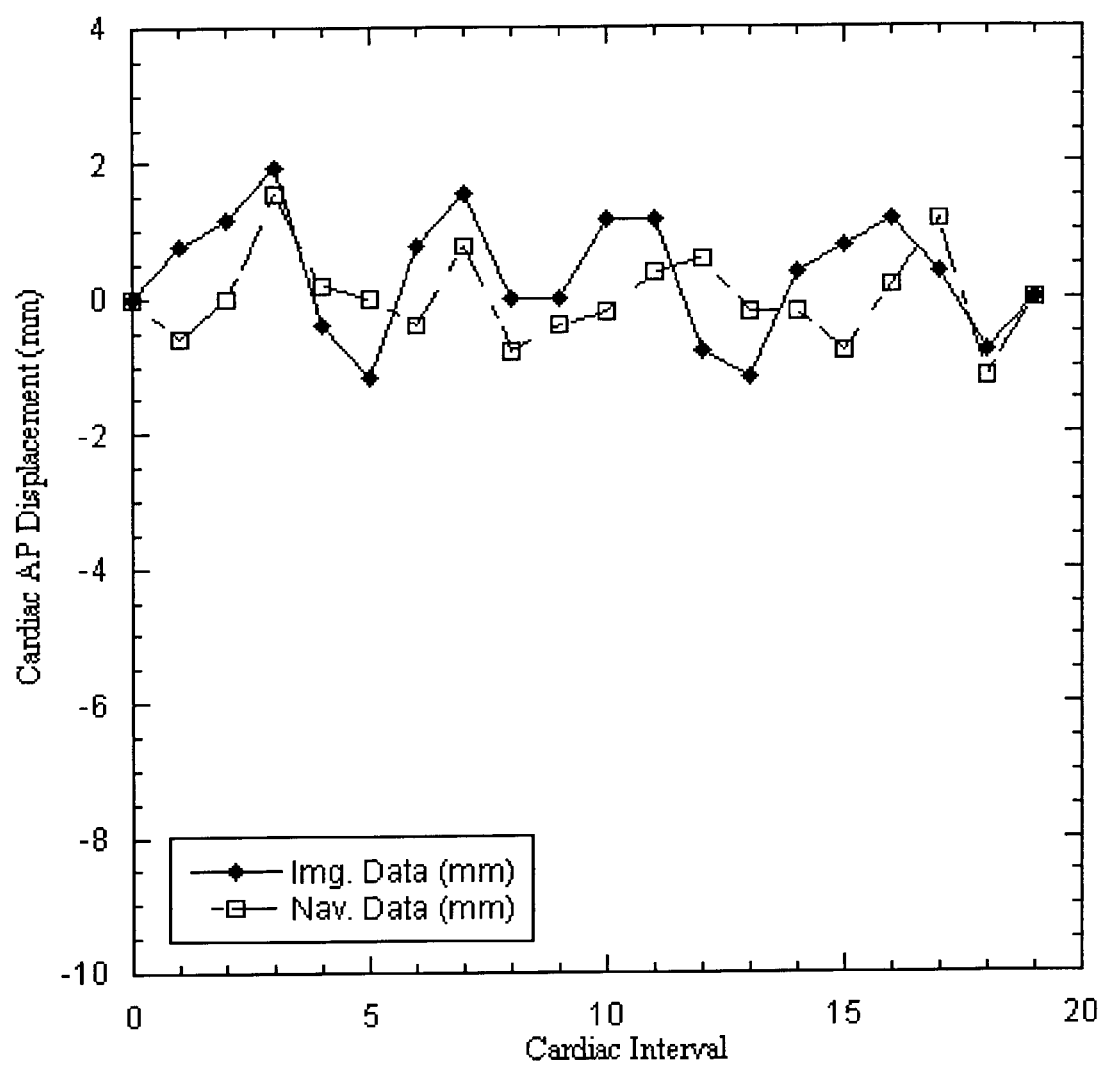
FIG. 13 is a plot of the AP displacement of the heart position for a free breathing condition as predicted by the RaMP navigators (LR flow encoding), and as calculated from the images obtained through the imaging sequence.

FIG. 12 compares the AP displacement of the heart position for a breath-hold condition as predicted by the RaMP navigators (SI-flow encoding), and as calculated from the images obtained through the imaging sequence. FIG. 13 compares the AP displacement of the heart position for a free breathing condition as predicted by the RaMP navigators (SI flow encoding), and as calculated from the images obtained through the imaging sequence. The capability of the RaMP navigators to predict the AP direction motion is determined by comparing the motion predicted by the navigators with that obtained from the imaging sequence, similar to the approach used in the SI motion study. The low resolution of the imaging sequence can introduce errors for estimating AP motion as compared to SI motion, due to the lower range of AP motion values. In spite of this, there is a reasonably good correlation between the motion predicted by the navigators for the breath-holding case, and the motion observed with the imaging scans. Both methods estimate the AP motion of the heart to be between 0 and 1 mm.

Even for the free-breathing case, there is good correlation between the AP motion predicted by the RaMP navigators and that obtained with the imaging sequence. As shown in the Bland-Altman plot for the free breathing case (FIG. 13), both the navigator and the imaging sequence estimate the AP motion of the heart to be in the range of −1.157 and 1.54 mm.

Figure 14:
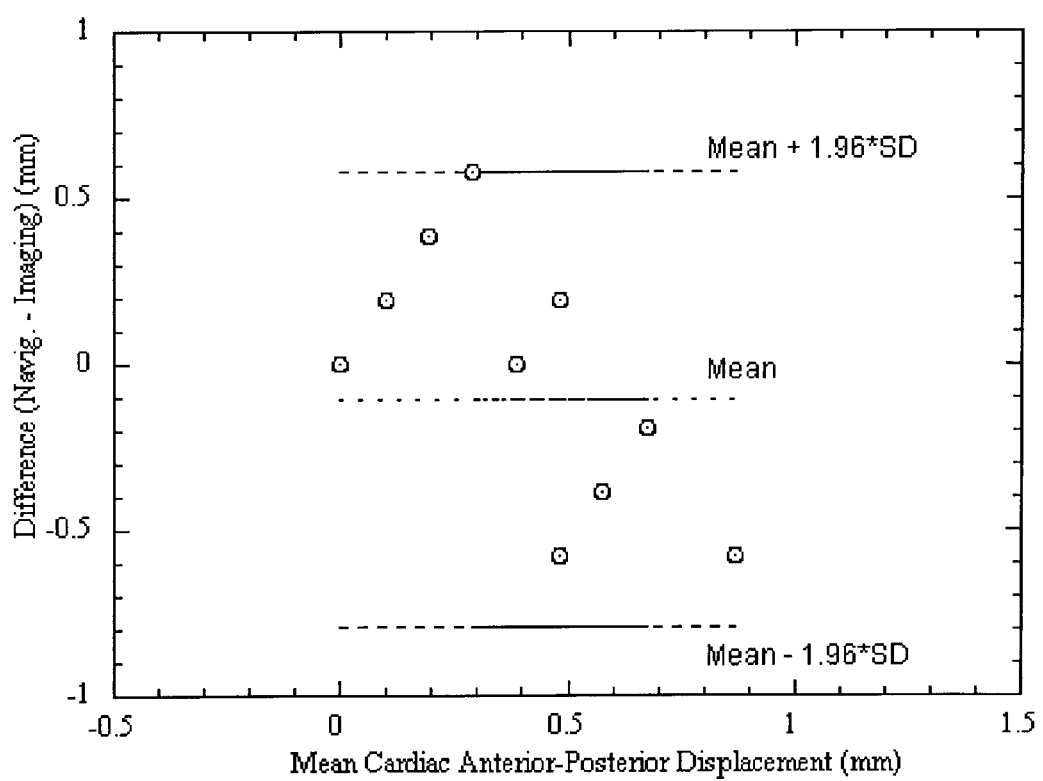
FIG. 14 is a Bland-Altman plot comparing the cardiac AP displacement for a breath-hold condition, as predicted by the RaMP navigators, and as calculated from the images obtained through the imaging sequence.
Figure 15:
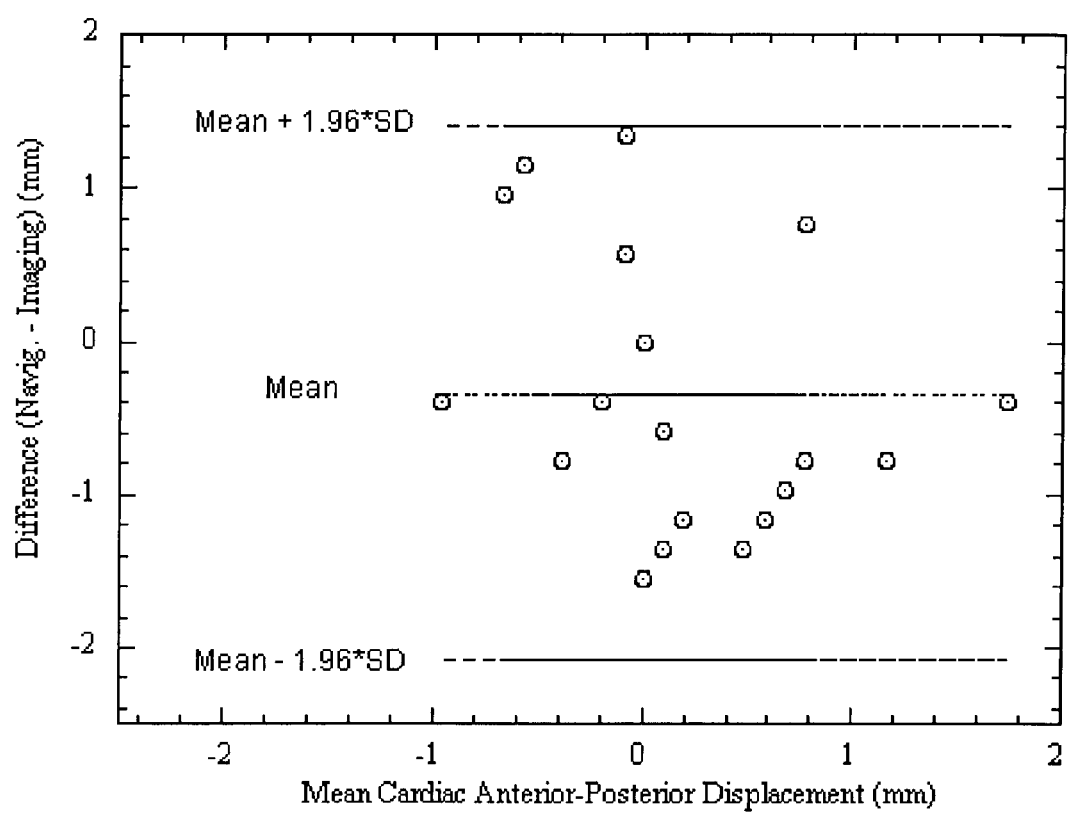
FIG. 15 is a Bland-Altman plot comparing the AP displacement for a free breathing condition, as predicted by the RaMP navigators, and as calculated from the images obtained through the imaging sequence.

FIGS. 14 and 15, respectively, show the Bland-Altman plots comparing AP displacement as predicted by the navigators, and as obtained from the imaging scan, for the breath-hold and free breathing cases. FIG. 14 shows a non-significant bias of the imaging measurements as compared to the navigator measurements. In this case, the bias is −0.106 mm, while the lower and upper 95% acceptance bounds are −0.794 mm and 0.582 mm respectively. FIG. 15 shows that there is a small bias of the imaging measurements as compared to the navigator measurements. In this case, the bias is −0.338 mm, while the lower and upper 95% acceptance bounds are −2.076 mm and 1.401 mm respectively.

From these particular tests, the accuracy of the RaMP approach in predicting bulk motion was determined to be ±1.22 mm in the SI direction and ±0.89 mm in the AP direction during normal breathing. The standard error for the free-breathing SI direction measurement was ±1.19 mm, while that for the AP direction measurement was ±0.17 mm. These values are merely illustrative of the accuracy that can be achieved with the disclosed methods.

Example 3

Prospective Application of Navigator Signals

Figure 16:
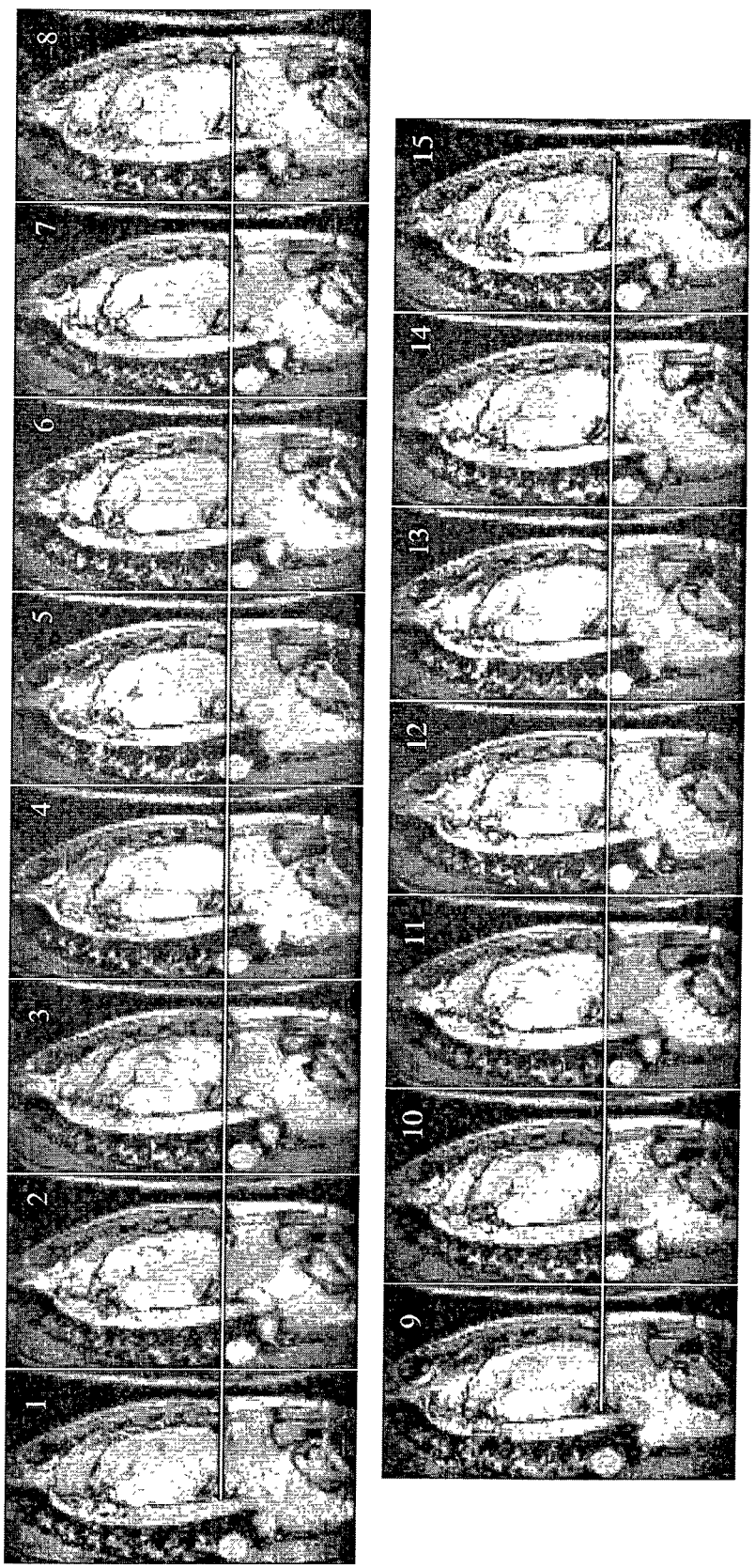
FIG. 16 is a series of prospectively navigated imaging scans for a first human subject over 15 cardiac cycles. The marker line illustrates the stationary nature of the heart. The motion of the imaging slice may be seen by following the displacement of the agarose tube phantom in the left-inferior section of the images.
Figure 18:
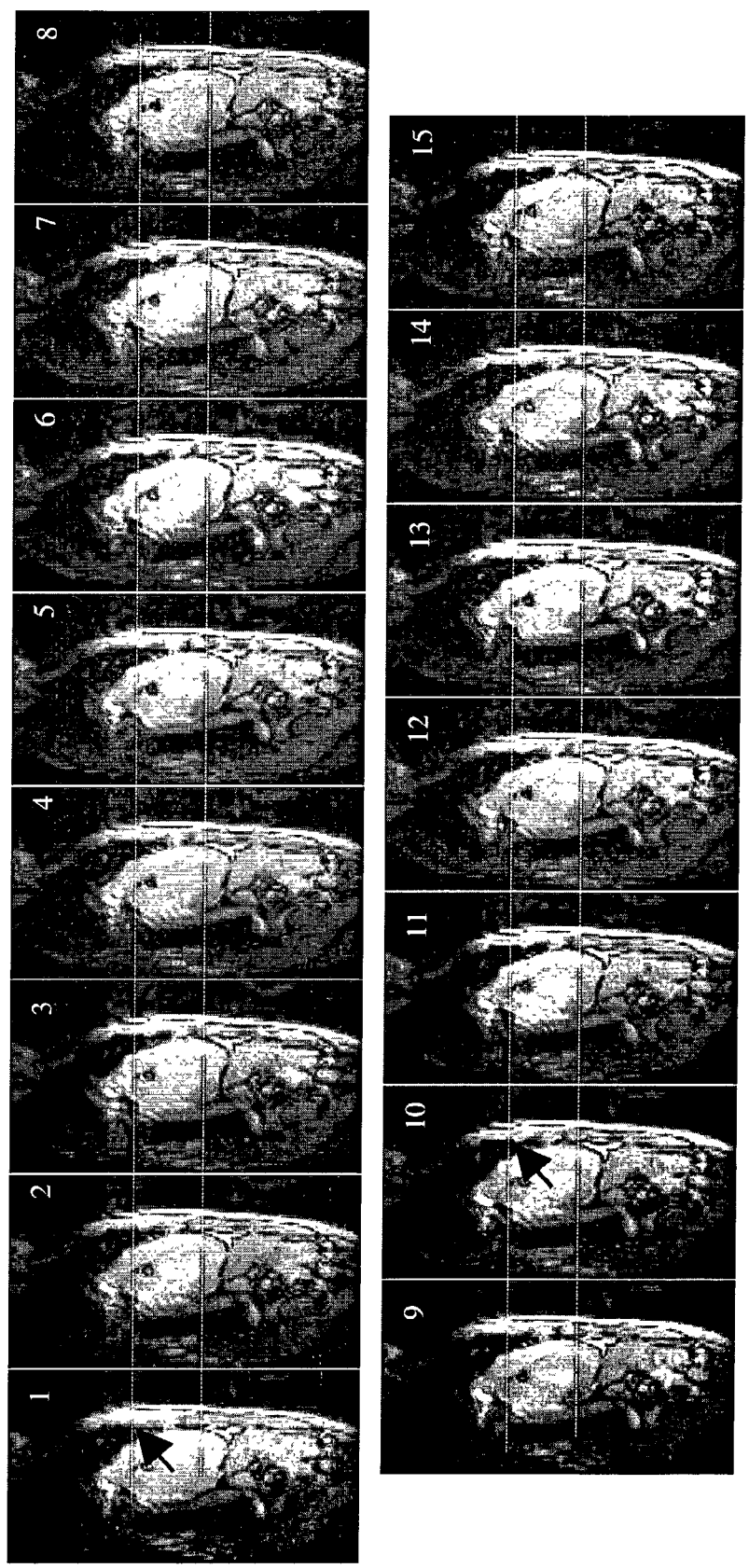
FIG. 18 is a series of prospectively navigated imaging scans for a second human subject over 15 cardiac cycles. The marker lines illustrate the stationary nature of the heart and the displacement of the chest wall due to the motion of the imaging slice. The reader can track the notch in the chest wall as indicated by the dark arrows in cycle 2 and cycle 10, in combination with the upper marker line to monitor the chest wall displacement. The lower marker line indicates the stationary position of the left ventricle wall.

In this example, a prospective navigator approach was implemented on the clinical scanner described in Example 2 above earlier. FIGS. 16 and 18, respectively, show the RaMP implementation on two different human volunteers (Case I and Case II). These figures show the cardiac position over 15 successive cardiac cycles. Marker lines are drawn through the figures to illustrate the shift in position of the various organs, and the absence of heart motion.

In Case I (FIG. 16), an agarose-filled tube was placed above the phased-array surface coil, in order to track the motion correction determined from the RaMP implementation. The marker line drawn through the apex of the heart shows the motion of the tube and the various organs, and also shows that the heart appears stationary during the entire imaging cycle (15 heartbeats). The stationary nature of the heart image and the motion of the imaging slice can be tracked by monitoring the displacement of the agarose tube phantom in the left-inferior section of the images.

In case II (FIG. 18), prospectively navigated imaging scans were also taken over 15 cardiac cycles. The marker lines illustrate the stationary nature of the heart image, and the displacement of the chest wall image due to the prospective motion of the imaging slice. For example, the notch in the chest wall indicated by the dark arrows in cycle 2 and cycle 10, and the upper marker line that monitors the chest wall displacement may be compared. The lower marker line indicates the stationary position of the left ventricle wall.

Figure 17:
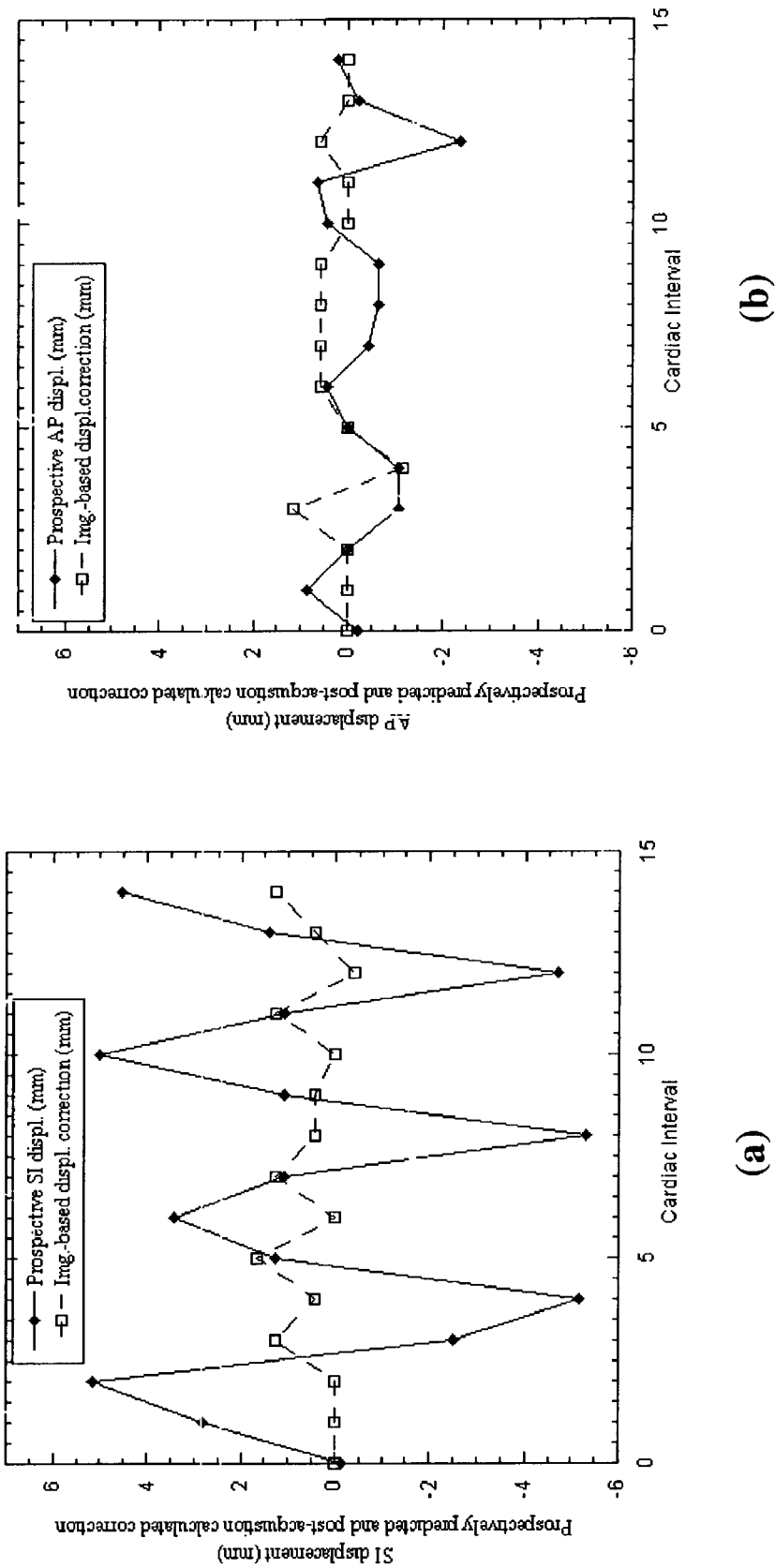
FIG. 17 is a pair of graphs comparing the cardiac SI and AP motions as predicted by the RaMP navigators, and as predicted by post-processed images for a first human subject under free-breathing (a) and breath-hold (b) conditions.

In order to determine the accuracy of the prospective navigation, prospectively aligned images were post-processed to determine whether there was any displacement correction required between the successive images. FIG. 17 shows the navigator-predicted displacement in the SI and the AP directions for case I, along with the displacement correction suggested in both directions. The amplitude of the residual correction is ±0.64 mm in SI and ±0.52 mm in the AP direction.

Figure 19:
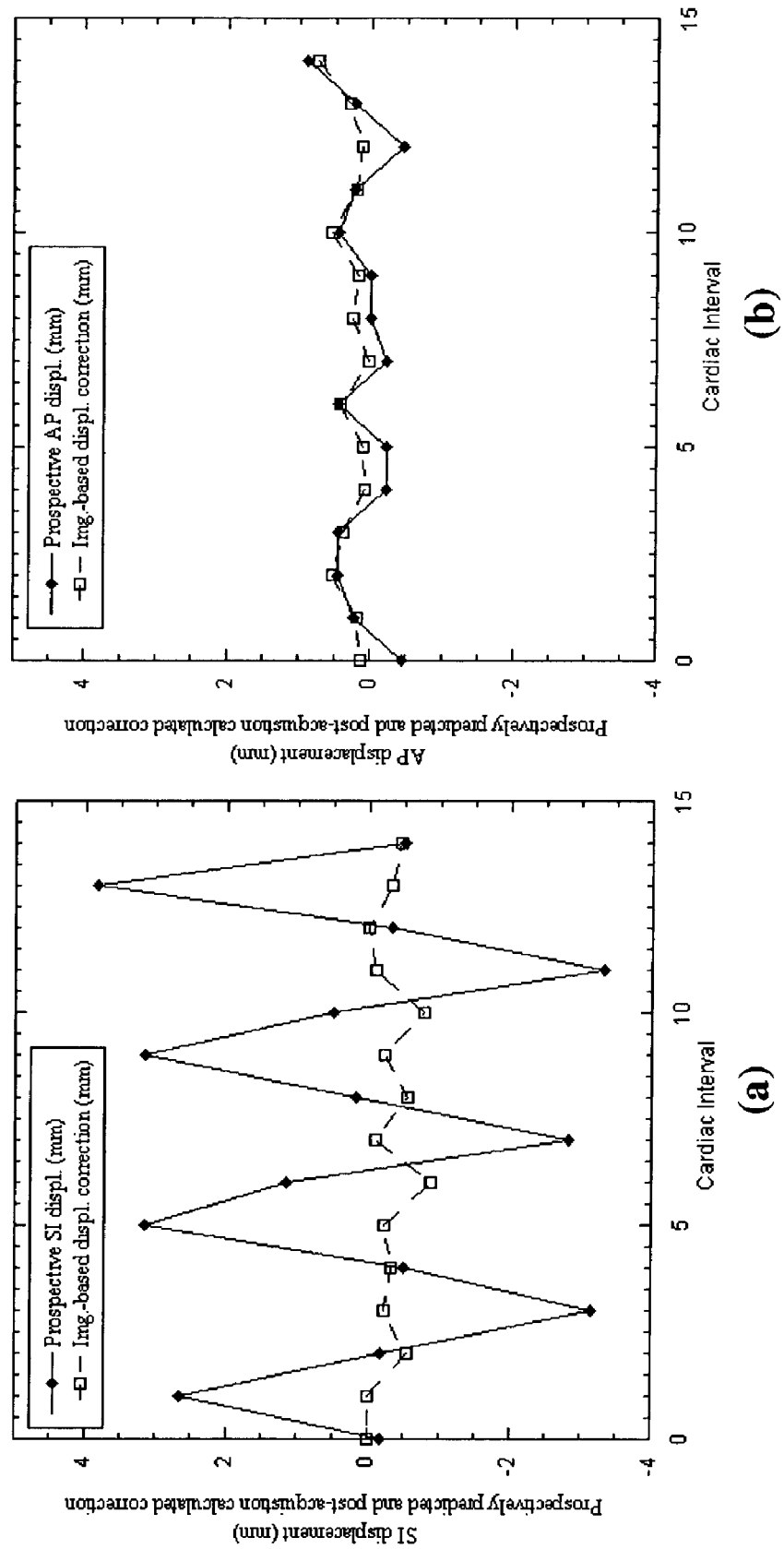
FIG. 19 is a pair of graphs showing the SI and AP motions as predicted by the navigators and from post-processed images for a second human subject under free-breathing (a) and breath-hold (b) conditions.

In Case II (FIG. 19), a smaller field-of-view is considered, and the marker line again illustrates that the various organs are displaced over the various cardiac cycles, while the heart remains stationary. The respiratory displacements are smaller in this volunteer as compared to the volunteer in Case I. FIG. 19 shows the navigator-predicted displacement in the SI and the AP directions, along with the displacement correction suggested in both directions, for Case II. The amplitude of the residual correction is ±0.28 mm in SI and ±0.21 mm in the AP direction. Both cases I and II illustrate that the prospective implementation of RaMP navigators is able to predict, and correct for, the bulk motion of the heart over multiple cardiac cycles to within 0.64 mm in the SI direction and ±0.52 mm in the AP direction.

Example 4

Computer Environments

I. Exemplary Distributed Computing Environment

Figure 20:
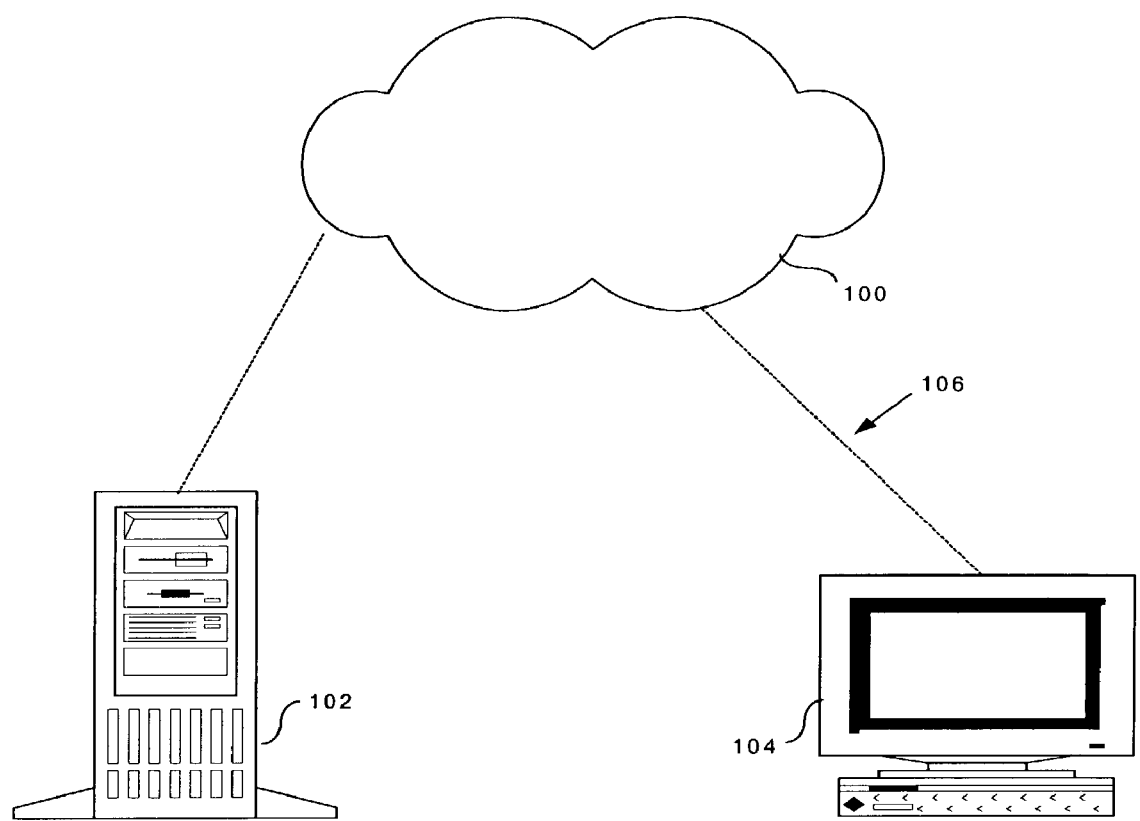
FIG. 20 is a diagram of a distributed computing environment in which the disclosed methods can be implemented.

FIG. 20 illustrates a distributed computing environment in which the software elements used to implement the disclosed navigator methods may reside. The distributed computing environment 100 includes two computer systems 102, 104 connected by a connection medium 106. The computer systems 102, 104 can be any of several types of computer system configurations, including personal computers, multiprocessor systems, and the like. In terms of logical relation with other computer systems, a computer system can be a client, a server, a router, a peer device, or other common network node. Moreover, although FIG. 20 illustrates two computer systems 102, 104, the figure is equally applicable to an arbitrary, larger number of computer systems connected by the connection medium 106. Additional computer systems 102 or 104 may be connected by an arbitrary number of connection mediums 106. The connection medium 106 can comprise any local area network (LAN), wide area network (WAN), or other computer network, including but not limited to Ethernets, enterprise-wide computer networks, intranets and the Internet.

Portions of the navigator software can be implemented in a single computer system 102 or 104, with the application later distributed to other computer systems 102, 104 in the distributed computing environment 100. Portions of the navigator software may also be practiced in a distributed computing environment 100 where tasks are performed by a single computer system 102 or 104 acting as a remote processing device that is accessed through a communications network, with the distributed application later distributed to other computer systems in the distributed computing environment 100. In a networked environment, program modules comprising the navigator software can be located on more than one computer system 102 or 104. Communication between the computer systems in the distributed computing network may advantageously include encryption of the communicated data.

II. Exemplary Computer System

Figure 21:
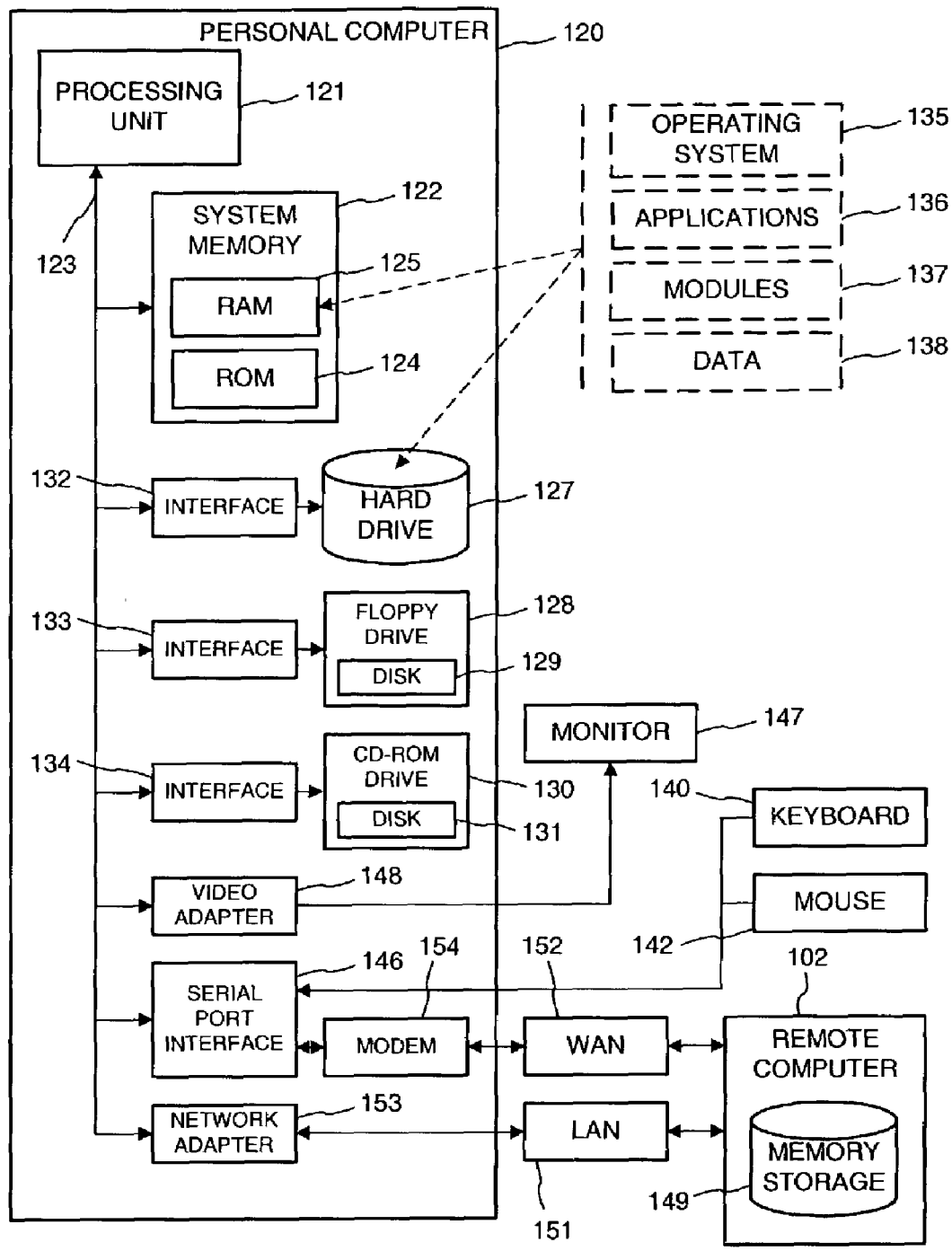
FIG. 21 is a block diagram of a computer system that can be used to implement the disclosed methods.

FIG. 21 illustrates an example of a computer system 120 that can serve as an operating environment for the navigator software. With reference to FIG. 21, an exemplary computer system for implementing the disclosed methods includes a computer 120 (such as a personal computer, laptop, palmtop, set-top, server, mainframe, and other varieties of computer), including a processing unit 121, a system memory 122, and a system bus 123 that couples various system components including the system memory to the processing unit 121. The processing unit can be any of various commercially available processors, including Intel x86, Pentium and compatible microprocessors from Intel and others, including Cyrix, AMD and Nexgen; Alpha from Digital; MIPS from MIPS Technology, NEC, IDT, Siemens, and others; and the PowerPC from IBM and Motorola. Dual microprocessors and other multi-processor architectures also can be used as the processing unit 121.

The system bus can be any of several types of bus structure including a memory bus or memory controller, a peripheral bus, and a local bus using any of a variety of conventional bus architectures such as PCI, VESA, AGP, Microchannel, ISA and EISA, to name a few. The system memory includes read only memory (ROM) 124 and random access memory (RAM) 125. A basic input/output system (BIOS), containing the basic routines that help to transfer information between elements within the computer 120, such as during start-up, is stored in ROM 124.

The computer 120 further includes a hard disk drive 127, a magnetic disk drive 128, e.g., to read from or write to a removable disk 129, and an optical disk drive 130, e.g., for reading a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of data, data structures, computer-executable instructions, etc. for the computer 120. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

A number of the navigator program modules can be stored in the drives and RAM 125, including an operating system 135, one or more application programs 136, other program modules 137, and program data 138.

A user can enter commands and information into the computer 120 through a keyboard 140 and pointing device, such as a mouse 142. Other input devices (not shown) can include a microphone, satellite dish, scanner, or the like. These and other input devices are often connected to the processing unit 121 through a serial port interface 146 that is coupled to the system bus, but can be connected by other interfaces, such as a parallel port, game port or a universal serial bus (USB). A monitor 147 or other type of display device is also connected to the system bus 123 via an interface, such as a video adapter 148. In addition to the monitor, computers typically include other peripheral output devices (not shown), such as printers.

The computer 120 can operate in a networked environment using logical connections to one or more other computer systems, such as computer 102. The other computer systems can be servers, routers, peer devices or other common network nodes, and typically include many or all of the elements described relative to the computer 120, although only a memory storage device 149 has been illustrated in FIG. 21. The logical connections depicted in FIG. 21 include a local area network (LAN) 151 and a wide area network (WAN) 152. Such networking environments are common in offices, enterprise-wide computer networks, intranets and the Internet.

When used in a LAN networking environment, the computer 120 is connected to the local network 151 through a network interface or adapter 153. When used in a WAN networking environment, the computer 120 typically includes a modem 154 or other means for establishing communications (e.g., via the LAN 151 and a gateway or proxy server 155) over the wide area network 152, such as the Internet. The modem 154, which can be internal or external, is connected to the system bus 123 via the serial port interface 146. In a networked environment, program modules depicted relative to the computer 120, or portions thereof, can be stored in the remote memory storage device. It will be appreciated that the network connections shown are exemplary and other means of establishing a communications link between the computer systems (including an Ethernet card, ISDN terminal adapter, ADSL modem, 10BaseT adapter, 100BaseT adapter, ATM adapter, or the like) can be used.

In accordance with the practices of persons skilled in the art of computer programming, a particular embodiment of the navigator method is described in FIG. 3 with reference to acts and symbolic representations of operations that may be performed by the computer 120. Such acts and operations are sometimes referred to as being computer-executed. It will be appreciated that the acts and symbolically represented operations include the manipulation by the processing unit 121 of electrical signals representing data bits which causes a resulting transformation or reduction of the electrical signal representation, and the maintenance of data bits at memory locations in the memory system (including the system memory 122, hard drive 127, floppy disks 129, and CD-ROM 131) to thereby reconfigure or otherwise alter the computer system's operation, as well as other processing of signals. The memory locations where data bits are maintained are physical locations that have particular electrical, magnetic, or optical properties corresponding to the data bits.

In view of the many possible embodiments to which the principles of the illustrated methods may be applied, it should be recognized that the particular embodiments described above are only specific examples of the invention and should not be taken as a limitation on the scope of the invention. Rather, the scope of the invention is defined by the following claims. We therefore claim as our invention all that comes within the scope and spirit of these claims.

We claim:

1. A method for correcting a magnetic resonance image for subject motion during image acquisition, comprising:
   exciting a volume within a subject with a flow encoded pulse sequence;
   detecting a flow-sensitive signal associated with blood flow within the volume of the subject;
   identifying a reference position within the volume based on the flow-sensitive signal; and
   using the reference position as a navigator for tracking and correcting for subject motion between image acquisition events.

2. The method of claim 1, wherein the volume excited is a volume that includes at least a portion of the left ventricle of the heart.

3. The method of claim 2, wherein exciting occurs at mid-systole or mid-diastole.

4. The method of claim 1, wherein the flow encoded pulse sequence comprises a bipolar velocity-encoding gradient.

5. The method of claim 4, wherein the flow encoded pulse sequence comprises a FLASH sequence incorporating the bipolar velocity-encoding gradient.

6. The method of claim 4, wherein detecting comprises calculating the complex difference between a transverse magnetization detected after a first bipolar velocity encoding gradient, and a transverse magnetization detected after a second bipolar gradient.

7. The method of claim 1, wherein the reference position is used to prospectively shift a position of a subsequent k-space imaging slice to compensate for subject motion between a first imaging sequence of pulses and a second imaging sequence of pulses.

8. A method for correcting a magnetic resonance image of the heart for subject motion during image acquisition, comprising:
   exciting a region of a subject including at least a portion of the blood volume of the heart with a flow-encoded pulse sequence;
   detecting a signal associated with blood flow in the heart based on the flow-encoded pulse sequence;
   determining a position associated with blood flow in the heart based on the detected signal; and
   using the determined position as a reference position for correcting the image of the heart for subject motion during image acquisition.

9. The method of claim 8, wherein the volume excited is a volume that includes at least a portion of the left ventricle of the heart.

10. The method of claim 9, wherein exciting occurs at mid-systole or mid-diastole.

11. The method of claim 8, wherein the flow-encoded pulse sequence comprises a bipolar velocity-encoding gradient.

12. The method of claim 11, wherein the flow-encoded pulse sequence comprises a FLASH sequence incorporating the bipolar velocity-encoding gradient.

13. The method of claim 11, wherein the detecting comprises calculating the complex difference between a transverse magnetization detected after a first bipolar velocity encoding gradient, and a transverse magnetization detected after a second bipolar gradient.

14. The method of claim 8, wherein the reference position is used to prospectively shift a position of a subsequent k-space imaging slice to compensate for subject motion between a first imaging sequence of pulses and a second imaging sequence of pulses.

15. A method for correcting for subject motion in an MRI image, comprising:
   exciting a volume within a subject with a flow-encoded pulse sequence;
   detecting a flow-sensitive signal associated with fluid flow in the volume;
   calculating a current position within the volume based on the detected signal relative to a reference position previously established based on a reference flow-sensitive signal; and
   translating a subsequent imaging slice to compensate for a difference between the current and reference positions.

16. The method of claim 15, wherein the volume includes at least a portion of the blood volume of the heart.

17. The method of claim 16, wherein exciting is timed relative to an ECG signal to occur at mid-systole or mid-diastole.

18. The method of claim 15, wherein the detecting comprises calculating the complex difference between a transverse magnetization detected after a first bipolar velocity encoding gradient, and a transverse magnetization detected after a second bipolar gradient.

19. The method of claim 18, wherein calculating a current position relative to a reference position comprises applying a one-dimensional Fast Fourier transform to a complex difference calculated for the reference flow-sensitive signal to provide a reference spectrum, applying a one-dimensional Fast Fourier transform to the current flow-sensitive signal to provide a current spectrum, multiplying the current spectrum with a mirror image of the reference spectrum to provide a product, and applying a Fast Fourier transform to the product to provide a measure of the difference between the current and reference positions.

20. An MRI system, comprising:
a magnet for producing a polarizing magnetic field;
an RF system for exciting spins in a subject positioned in the polarizing magnetic field;
a gradient system for producing magnetic field gradients in the subject;
a pulse generator connected to the RF system and the gradient system and capable of providing a flow-encoded pulse sequence; and
a computer system, the computer system having stored thereon computer-executable instructions for generating a blood flow-sensitive navigator signal and for shifting an imaging slice in response to a change in position of the subject based on the blood flow sensitive navigator signal.

21. An MRI system, comprising:
a magnet for producing a polarizing magnetic field;
an RF system for exciting spins in a subject positioned in the polarizing magnetic field;
a gradient system for producing magnetic field gradients in the subject;
a pulse generator connected to the RF system and the gradient system and capable of providing a flow-encoded pulse sequence; and
a computer system, the computer system having stored thereon computer-executable instructions for carrying out the method comprising:
exciting a volume within a subject with a flow-encoded pulse sequence;
detecting a flow-sensitive signal associated with blood flow within the volume of the subject;
identifying a reference position within the volume based on the flow-sensitive signal; and
using the reference position as a navigator for tracking subject motion between image acquisition events.

22. A computer-readable medium having stored thereon computer-executable instructions for implementing a method comprising:
exciting a volume within a subject with a flow-encoded pulse sequence;
detecting a flow-sensitive signal associated with blood flow within the volume of the subject;
identifying a reference position within the volume based on the flow-sensitive signal; and
using the reference position as a navigator for tracking subject motion between image acquisition events.

23. A computer-readable medium having stored thereon computer-executable instructions for implementing a method comprising:
exciting a region of a subject including at least a portion of the blood volume of the heart with a flow-encoded pulse sequence;
detecting a signal associated with blood flow in the heart at a position within the region of the subject excited by the flow-encoded pulse sequence; and
using the position of the signal as a reference position for correcting the image of the heart for subject motion during image acquisition.

24. A computer-readable medium having stored thereon computer-executable instructions for implementing a method comprising:
exciting a volume within a subject with a flow-encoded pulse sequence;
detecting a flow-sensitive signal associated with fluid flow in the volume;
calculating a current position within the volume based on the detected signal relative to a reference position previously established based on a reference flow-sensitive signal; and
translating a subsequent imaging slice to compensate for a difference between the current and reference positions.

25. A method for compensating subject motion in an MRI image, comprising:
exciting a volume within a subject with a motion-encoded pulse sequence;
detecting a motion-sensitive signal associated with subject motion in the volume based on the motion-encoded pulse sequence;
calculating a current position within the volume based on the detected motion sensitive-signal relative to a reference position; and
compensating a subsequent imaging slice based on a difference between the current and reference positions.

26. The method of claim 25, wherein the excited volume includes at least a portion of the left ventricle of the heart.

27. The method of claim 26, wherein exciting occurs at mid-systole or mid-diastole.

28. The method of claim 25, wherein the motion-encoded pulse sequence comprises a bipolar velocity-encoding gradient.

29. The method of claim 28, wherein the motion-encoded pulse sequence comprises a FLASH sequence incorporating the bipolar velocity-encoding gradient.

30. The method of claim 28, wherein the current position within the volume is calculated with respect to the reference position based on a complex difference between a transverse magnetization detected after a first bipolar velocity-encoding gradient, and a transverse magnetization detected after a second bipolar velocity-encoding gradient.

31. The method of claim 25, further comprising prospectively shifting a position of a subsequent imaging slice to compensate for subject motion between a first imaging sequence and a second imaging sequence.

* * * * *